(12) United States Patent
Ameer et al.

(10) Patent No.: US 12,214,104 B2
(45) Date of Patent: Feb. 4, 2025

(54) PHOTO-REACTIVE INKS AND THERMAL-CURABLE MATERIALS MADE THEREFROM

(71) Applicant: Northwestern University, Evanston, IL (US)

(72) Inventors: Guillermo A. Ameer, Chicago, IL (US); Henry Oliver Tenadooah Ware, Evanston, IL (US); Cheng Sun, Wilmette, IL (US); Congwen Duan, Wilmette, IL (US)

(73) Assignee: Northwestern University, Evanston, IL (US)

( * ) Notice: Subject to any disclaimer, the term of this patent is extended or adjusted under 35 U.S.C. 154(b) by 384 days.

(21) Appl. No.: 16/646,848

(22) PCT Filed: Sep. 13, 2018

(86) PCT No.: PCT/US2018/050887
§ 371 (c)(1),
(2) Date: Mar. 12, 2020

(87) PCT Pub. No.: WO2019/055656
PCT Pub. Date: Mar. 21, 2019

(65) Prior Publication Data
US 2021/0008246 A1 Jan. 14, 2021

Related U.S. Application Data

(60) Provisional application No. 62/557,982, filed on Sep. 13, 2017.

(51) Int. Cl.
*A61L 27/16* (2006.01)
*A61L 27/04* (2006.01)
(Continued)

(52) U.S. Cl.
CPC ............. *A61L 27/16* (2013.01); *A61L 27/047* (2013.01); *A61L 27/10* (2013.01); *A61L 27/12* (2013.01);
(Continued)

(58) Field of Classification Search
CPC ........ A61L 27/16; A61L 27/047; A61L 27/10; A61L 27/12; A61L 27/58;
(Continued)

(56) References Cited

U.S. PATENT DOCUMENTS 5,184,307 A 2/1993 Hull et al.
5,236,637 A 8/1993 Hull
(Continued)

FOREIGN PATENT DOCUMENTS

WO WO-9731971 A1 * 9/1997 ........... A61L 15/425
WO WO 2016/176444 11/2016
(Continued)

OTHER PUBLICATIONS

International Search Report and Written Opinion for PCT/US18/50887. Mailed Nov. 15, 2018. 16 pages.
(Continued)

*Primary Examiner* — Nahida Sultana
(74) *Attorney, Agent, or Firm* — David W. Staple; Casimir Jones, S.C.

(57) ABSTRACT

Provided herein photo-reactive inks, thermal-curable materials and objects (e.g., medical implants, scaffolds, devices, etc.) made therefrom, and methods of preparation and use thereof.

17 Claims, 8 Drawing Sheets

(51) Int. Cl.

| | | |
|---|---|---|
| *A61L 27/10* | (2006.01) | |
| *A61L 27/12* | (2006.01) | |
| *A61L 27/58* | (2006.01) | |
| *B29C 35/02* | (2006.01) | |
| *B29C 64/124* | (2017.01) | |
| *B29C 64/30* | (2017.01) | |
| *B33Y 10/00* | (2015.01) | |
| *B33Y 40/20* | (2020.01) | |
| *B33Y 70/10* | (2020.01) | |
| *B33Y 80/00* | (2015.01) | |

(52) U.S. Cl.
CPC ............. *A61L 27/58* (2013.01); *B29C 35/02* (2013.01); *B29C 64/124* (2017.08); *B29C 64/30* (2017.08); *B33Y 10/00* (2014.12); *B33Y 40/20* (2020.01); *B33Y 70/10* (2020.01); *A61L 2300/802* (2013.01); *A61L 2430/02* (2013.01); *B33Y 80/00* (2014.12)

(58) Field of Classification Search
CPC ........... A61L 2300/802; A61L 2430/02; A61L 2400/12; A61L 27/54; B29C 35/02; B29C 64/124; B29C 64/30; B29C 71/02; B33Y 10/00; B33Y 40/20; B33Y 70/00; B33Y 80/00
See application file for complete search history.

(56) References Cited

U.S. PATENT DOCUMENTS

| | | | |
|---|---|---|---|
| 6,936,212 B1* | 8/2005 | Crawford | B29C 41/36 264/401 |
| 8,404,264 B2 | 3/2013 | Ameer et al. | |
| 8,568,765 B2 | 10/2013 | Ameer et al. | |
| 8,580,912 B2 | 11/2013 | Ameer et al. | |
| 8,758,796 B2 | 6/2014 | Ameer et al. | |
| 8,772,437 B2 | 7/2014 | Ameer et al. | |
| 8,911,720 B2 | 12/2014 | Ameer et al. | |
| 8,992,967 B2 | 3/2015 | Ameer et al. | |
| 9,360,757 B2 | 6/2016 | Desimone et al. | |
| 10,758,456 B2* | 9/2020 | Moser | C08F 222/1025 |
| 11,390,016 B2* | 7/2022 | Osiroff | B29C 33/3842 |
| 11,390,705 B2* | 7/2022 | Poelma | C08J 3/12 |
| 2003/0118692 A1 | 6/2003 | Wang et al. | |
| 2007/0088444 A1* | 4/2007 | Hodorek | A61F 2/30756 623/23.61 |
| 2009/0325859 A1 | 12/2009 | Ameer et al. | |
| 2013/0211500 A1 | 8/2013 | Kibbe et al. | |
| 2014/0037588 A1 | 2/2014 | Yang et al. | |
| 2014/0058049 A1 | 2/2014 | Ameer et al. | |
| 2014/0135407 A1 | 5/2014 | Ameer et al. | |
| 2014/0155516 A1 | 6/2014 | Ameer et al. | |
| 2016/0167323 A1* | 6/2016 | Valeri | B29D 11/00432 264/2.6 |
| 2016/0369040 A1* | 12/2016 | Das | C08L 63/00 |
| 2018/0236122 A1 | 8/2018 | Xiao et al. | |
| 2022/0133958 A1* | 5/2022 | Akar | A61L 31/129 424/78.17 |

FOREIGN PATENT DOCUMENTS

| | | | | |
|---|---|---|---|---|
| WO | WO 2016/183277 | | 11/2016 | |
| WO | WO-2017078883 A1 * | 5/2017 | ........... | A61K 6/0023 |

OTHER PUBLICATIONS

Arshady, Preparation of biodegradable microspheres and microcapsules:2. Polyactides and related polyesters. J. Controlled Release. 1991. 17:1-22.

Bártolo, Stereolithography: materials, processes, and applications. 2011: Springer Science & Business Media.

Bose et al., Recent advances in bone tissue engineering scaffolds. Trends Biotechnol. Oct. 2012;30(10):546-54.

Choi et al., Multi-material stereolithography. Journal of Materials Processing Technology, 2011. 211(3): p. 318-328.

David et al., Hydroxyapatite cement in pediatric craniofacial reconstruction. J Craniofac Surg. Jan. 2005;16(1):129-33.

Giannatsis et al., Additive fabrication technologies applied to medicine and health care: a review. The International Journal of Advanced Manufacturing Technology, 2009. 40(1-2): p. 116-127.

Holland et al., Polymers for biodegradable medical devices. 1. The potential of polyesters as controlled macramolecular release systems. J. Controlled Release. 1986. vol. 4:155-0180.

Illum, L., Davids, S. S. (eds.) "Polymers in Controlled Drug Delivery" Wright, Bristol, 1987.

Jakus et al., Hyperelastic "bone": A highly versatile, growth factor-free, osteoregenerative, scalable, and surgically friendly biomaterial. Sci Transl Med. Sep. 28, 2016;8(358):358ra127.

Jayanthi et al., Influence of Post Curing Conditions on the Mechanical Properties of Stereolithographic Photopolymers. Du Pont Somos Materials Group, Aug. 1995: 11 pages.

Kim et al., Stereolithographic bone scaffold design parameters: osteogenic differentiation and signal expression. Tissue Eng Part B Rev. Oct. 2010;16(5):523-39.

Laurencin et al., Bone graft substitutes. Expert Rev Med Devices. Jan. 2006;3(1):49-57.

Ma et al., A Thermally Responsive Injectable Hydrogel Incorporating Methacrylate-Polylactide for Hydrolytic Lability. Biomacromolecules. Jul. 12, 2010, vol. 11, No. 7 pp. 1873-1881.

Melchels et al., A review on stereolithography and its applications in biomedical engineering. Biomaterials. Aug. 2010;31(24):6121-30.

Pei, 4D printing—revolution or fad? Assembly Automation, 2014. 34(2): p. 123-127.

Pitt, The controlled parenteral delivery of polypeptides and proteinds. Int. J. Phar. 1990. vol. 59:173-196.

Qiu et al., A citric acid-based hydroxyapatite composite for orthopedic implants. Biomaterials. Dec. 2006;27(34):5845-54.

Serrano et al., Novel biodegradable shape-memory elastomers with drug-releasing capabilities. Adv Mater. May 17, 2011;23(19):2211-5.

Sun et al., Projection micro-stereolithography using digital micromirror dynamic mask. Sensors and Actuators A: Physical, 2005. 121(1): p. 113-120.

Tran et al., Citrate-Based Biomaterials and Their Applications in Regenerative Engineering. Annu Rev Mater Res. Jul. 2015;45:277-310.

Tumbleston et al., Additive manufacturing. Continuous liquid interface production of 3D objects. Science. Mar. 20, 2015;347(6228):1349-52.

Van Lith et al., 3D-Printing Strong High Resolution Antioxidant Bioresorbable Vascular Stents. Advanced Materials Technologies, 2016. 7 pages.

Wang et al. Photo-crosslinked Biodegradable Elastomers for Controlled Nitric Oxide Delivery. Biomater Sci. Jun. 2013;1(6):625-632.

Wicker et al., Multi-material, multi-technology stereolithography. Virtual and Physical Prototyping, 2012. 7(3): p. 181-194.

Xiao et al., A Cooperative Copper Metal-Organic Framework-Hydrogel System Improves Wound Healing in Diabetes. Adv Funct Mater. Jan. 5, 2017, vol. 27, No. 1.

Yang et al., A thermoresponsive biodegradable polymer with intrinsic antioxidant properties. Biomacromolecules, 2014. 15(11):3942-52.

Yang et al., Synthesis and evaluation of poly(diol citrate) biodegradable elastomers. Biomaterials. Mar. 2006;27(9):1889-98.

* cited by examiner

PHOTO-REACTIVE INKS AND THERMAL-CURABLE MATERIALS MADE THEREFROM

CROSS-REFERENCE TO RELATED APPLICATIONS

The present application claims priority to U.S. Provisional Patent Application No. 62/557,982, filed Sep. 13, 2017, which is incorporated by reference in its entirety.

FIELD

Provided herein photo-reactive inks, thermal-curable materials and objects (e.g., medical implants, scaffolds, devices, etc.) made therefrom, and methods of preparation and use thereof.

BACKGROUND

Tissue scaffolds are structures manufactured to provide mechanical support, during repair and regeneration of injured tissue (Ref. 1; incorporated by reference in its entirety). Bone scaffolds can be made from a wide variety of materials from polymers to ceramics to metals. Each individual material type has its strength and drawback. In particular ceramics have the strength, but their stiffness make them difficult to implement in surgery (Ref. 2; incorporated by reference in its entirety). Calcium phosphates such as hydroxyapatite (HA) are a major component in natural bone, which have made them widely studied as scaffold material (Ref. 1; incorporated by reference in its entirety). Composites of ceramics and polymers have arisen in recent years, which take advantage of both material types (Refs. 1-3; incorporated by reference in their entireties). Within composite scaffolds, HA can impart osteoconductivity to the surrounding polymer matrix (Refs. 4-6; incorporated by reference in their entireties). Citric acid is an important component in the body that is necessary for healthy bone formation (Ref. 7; incorporated by reference in its entirety). A class of biodegradable citric-acid-based biomaterials (CBBs) have been developed that are intrinsically antioxidant, anti-inflammatory, antimicrobial, and can be made to be vasculoinductive (Ref. 3; incorporated by reference in its entirety). CBB mechanical and degradation properties can be tailored to fit a variety of applications, depending on the polymerization method and chain length of monomer (Ref. 8; incorporated by reference in its entirety). Methacrylated polydiol citrates had previously been reported to be photopolymerizable (Ref. 9; incorporated by reference in its entirety), and methacrylated poly(1,12-dodecanediol citrate) (mPDC) can be 3D printed using photopolymerization methods (Ref. 10; incorporated by reference in its entirety).

3D printing, also known as additive manufacturing (AM), is a term used to describe several different processes that builds the user-designed CAD part layer-by-layer until completion (Ref. 11; incorporated by reference in its entirety). These processes include photopolymerization methods, extrusion-based methods, laser-induced melting/sintering, etc. 3D printing techniques give the designer geometric flexibility that is troublesome for standard subtractive manufacturing processes (Refs. 11, 12; incorporated by reference in their entireties). 3D printing has typically been used for small batch manufacturing, such as prototype manufacturing and biomedicine for patient specific needs. Typical methods for bone scaffold manufacture typically utilize powder bed methods, such as selective laser sintering and polyjet methods (Ref. 1; incorporated by reference in its entirety). Other methods include extrusion of ceramic slurries and stereolithography, which are more uncommon (Refs. 2, 13; incorporated by reference in their entireties). In recent years, there has been interest in 4D printing, which can be defined as 3D printing of objects or materials that have changing properties (geometric or mechanical) over time in response to an external stimulus (Ref. 14; incorporated by reference in its entirety).

Continuous liquid interface processing (CLIP) is an additive manufacturing process that utilizes photopolymerization to create 3D geometric parts. CLIP could be considered a 3rd generation of stereolithography AM process. Projection stereolithography (PSL; stereolithography 2nd generation) utilizes patterning the UV light via a dynamic mask generator to allow fabrication of each cross-sectional layer in a single exposure (Ref. 15; incorporated by reference in its entirety). In-plane resolution of PSL is dependent on the pixel size of the dynamic mask generator. In the case of projection microstereolithography (PuSL), in-plane resolution can be sub-20 um. With an emphasis on high precision and surface finish, a high resolution microCLIP process has recently been developed (Ref. 10; incorporated by reference in its entirety). CLIP/microCLIP works in similar manner to PSL with the addition of an air/oxygen permeable window placed between the UV light optics and the photopolymer resin. Oxygen is a natural inhibitor of the photopolymerization reaction. With introduction of oxygen permeable window into the UV light pathway allows a small region where no polymerization occurs (Ref. 16; incorporated by reference in its entirety). This allows removal of a "delamination" step during fabrication (removing polymerized layer from optical window). In addition, this small polymerization-free region allows new photoresin to flow in and replace polymerized material, allowing essentially continuous fabrication of each layer onto the previous layer until the part is complete. CLIP/microCLIP has caused a massive reduction in fabrication time within the stereolithography processes, which typically range from several hours to now several minutes (Refs 10, 16; incorporated by reference in their entireties). This process has opened the door to newer materials that may have been troublesome to utilize in previous stereolithography techniques, such as very viscous materials or materials that need quickly evaporating solvents.

SUMMARY

Provided herein photo-reactive inks, thermal-curable materials and objects (e.g., medical implants, scaffolds, devices, etc.) made therefrom, and methods of preparation and use thereof.

In particular embodiments, provided herein are materials and objects (e.g., medical implants, scaffolds, devices, etc.) the have initial elastic mechanical properties, which facilitates placement within a subject; however, upon implantation, due to body temperature, the material gradually hardens into a more rigid state. The materials, scaffolds, and methods herein find use, for example, in bone and/or soft tissue regeneration.

In some embodiments, provided herein are compositions comprising: (a) an acrylated or methacrylated polymer; (b) a photoinitiator, wherein exposure to light of an appropriate wavelength results in formation of a first reactive species from the photoinitiator; and (c) a thermal initiator, wherein exposure to heat results in in formation of a second reactive species from the thermal initiator. In some embodiments, the first reactive species and/or second reactive species is a free radical, cation, or anion. In some embodiments, the appropriate wavelength of light is in the UV range (e.g., 10-400 nm (e.g., 10 nm, 20 nm, 40 nm, 60 nm, 80 nm, 100 nm, 120 nm, 140 nm, 160 nm, 180 nm, 200 nm, 220 nm, 240 nm, 260 nm, 280 nm, 300 nm, 320 nm, 340 nm, 360 nm, 380 nm, 400 nm, or ranges therebetween)). In some embodiments, exposure to heat comprises increasing temperature above a threshold temperature. In some embodiments, exposure to heat comprises exposure to physiologic temperatures (e.g., 34-40° C. (e.g., about 37° C.)).

In some embodiments, compositions further comprise one or more additional polymeric, bioceramic (e.g., TCP), or nanostructured (e.g., MOF) components. In some embodiments, the acrylated or methacrylated polymer and the additional component are present at a ratio of between 1:10 and 10:1 (e.g., 1:10, 1:5, 3:10, 2:5, 1:2, 3:5, 7:10, 4:5, 9:10, 1:1, 10:9, 5:4, 10:7, 5:3, 2:1, 5:2, 10:3, 5:1, 10:1, or ranges therebetween). In some embodiments, the additional component is hydroxyapatite. In some embodiments, the additional component is TCP. In some embodiments, the additional component is an MOF (e.g., Cu MOF). In some embodiments, compositions further comprise a solvent (e.g., water, ethanol, methanol, etc.).

In some embodiments, the composition is a liquid. In some embodiments, the composition is an ink suitable for photoinitiated 3D printing. In some embodiments, exposure of the composition to the light of an appropriate wavelength results in crosslinking of the acrylated or methacrylated polymer, induced by the photoinitiator, to form a malleable solid material. In some embodiments, exposure of the malleable solid material to heat results in curing of the malleable solid material, induced by the thermal initiator, to form a thermoset material.

In some embodiments, the acrylated or methacrylated polymer is a biodegradeable and/or biocompatible polyester. In some embodiments, the acrylated or methacrylated polymer is a citric acid-based polyester. In some embodiments, the citric acid-based polyester comprises of polymer of citric acid and linear aliphatic diol monomers. In some embodiments, the citric acid-based polyester comprises a poly(diol citrate). In some embodiments, the diol is a linear aliphatic diol, X carbons in length, wherein X is between 2 and 20, and comprising OH groups on the 1 and X carbons. In some embodiments, the diol is selected from the group consisting of 1,4-butanediol, 1,6-hexanediol, 1,8-octanediol, 1,10-decanediol, 1,12-dodecanediol, 1,14-quattuordecanediol, and 1,16-sedecimanediol. In some embodiments, at least 10% of the citric acid monomers of the acrylated or methacrylated polymer display a methacrylate or acrylate (e.g., 10%, 20%, 30%, 40%, 50%, 60%, 70%, 80%, 90%, 95%, 99%, or more or ranges therebetween (e.g., 50-90%, 90% or more, etc.).

In some embodiments, the photoinitiator comprises a compound selected from the group consisting of azobisisobutyronitrile (AIBN), benzoyl peroxide, 2,2-Dimethoxy-2-phenylacetophenone (DMPA), camphorquinone (CQ), phenylbis(2,4,6-trimethylbenzoyl) phosphine oxide (BAPO), 2-Hydroxy-2-methylpropiophenone, ethyl 4-dimethylaminobenzoate (EDAB), and 2-hydroxy-4'-(2-hydroxyethoxy)-2-methylpropiophenone.

In some embodiments, the thermoresponsive initiator is a diazo compound. In some embodiments, the thermoresponsive initiator is selected from the group consisting of V-65, V-70, V-40, V-50, V-59, VA-044, VA-057, VA-061, VA-086, and BPO.

In some embodiments, provided herein are objects (e.g., medical implant, medical device, cell scaffold, etc.) generated by photoinitiated 3D printing using the compositions (e.g., 3D printing inks) described herein.

In some embodiments, provided herein are thermoset objects (e.g., medical implant, medical device, cell scaffold, etc.) and/or materials generated by thermally-induced curing of the malleable solid materials object and/or materials (e.g., produced by photoinitiated 3D printing using the inks described herein).

In some embodiments, provided herein are methods of stereolithographically printing a 3D object comprising: (a) depositing a layer of a ink described herein (e.g., comprising an acrylated or methacrylated polymer, a photoinitiator, and a thermal initiator); (b) exposing the layer to light of the appropriate wavelength to form the first reactive species from the photoinitiator, wherein the first reactive species induces crosslinking of the acrylated or methacrylated polymer to form a malleable solid material; (c) depositing an additional layer of the ink atop the previous layer; (d) exposing the additional layer to light of the appropriate wavelength to form the first reactive species from the photoinitiator, wherein the first reactive species induces crosslinking of the acrylated or methacrylated polymer to form a malleable solid material; and (e) repeating steps (c) and (d) sufficient number of times (e.g., 5, 10, 20, 30, 40, 50, 60, 70, 80, 90, 100, 150, 200, 250, 300, 400, 500, 600, 700, 800, 900, 1000, or more) to form the 3D object. In some embodiments, the depositing and exposing steps are performed by continuous liquid interface processing (CLIP), microsterolithography, or microCLIP. In some embodiments, provided herein are objects (e.g., medical implant, medical device, cell scaffold, etc.) produced by the stereolithographic printing methods described herein.

In some embodiments, provided herein are methods of curing a malleable solid object described herein into a fixed shape, position, and/or orientation, comprising: (a) manipulating the object into a desired shape, position, and/or orientation; and (b) exposing the object to sufficient heat to form the second reactive species from the thermal initiator, wherein the second reactive species induces curing of the malleable solid material to fix the object into the desired shape, position, and/or orientation. In some embodiments, the object is a medical implant or medical device, wherein manipulating the object comprising implanting the device into a subject, and wherein the sufficient heat is physiologic temperature of the subject. In some embodiments, provided herein are objects (e.g., medical implant, medical device, cell scaffold, etc.) fixed by the curing methods described herein.

In some embodiments, provided herein is the use of the compositions, methods, objects, etc. described herein in a medical procedure (e.g., implanting a medical implant, medical device, cell scaffold, etc. into a subject and fixing its shape, orientation, and/or position).

In some embodiments, provided herein are methods of promoting bone or tissue regeneration at a defect site in a subject comprising: (a) placing at the defect site a malleable solid implant generated by photoinitiated 3D printing using a composition described herein as an ink; and (b) allowing the implant to undergo thermally-induced curing within the subject to form a thermoset implant at the defect site. In some embodiments, methods further comprise exposure to UV light or incubation at elevated temperature prior to placing the malleable solid implant at the defect site. In some embodiments, pre-exposure to UV light or incubation at elevated temperature initiates but does not complete the formation of the thermoset implant prior to implantation. In some embodiments, the elevated temperature is 30-50° C. (e.g., 30° C., 35° C., 40° C., 45° C., 50° C., or ranges therebetween).

DEFINITIONS

Figure 1:
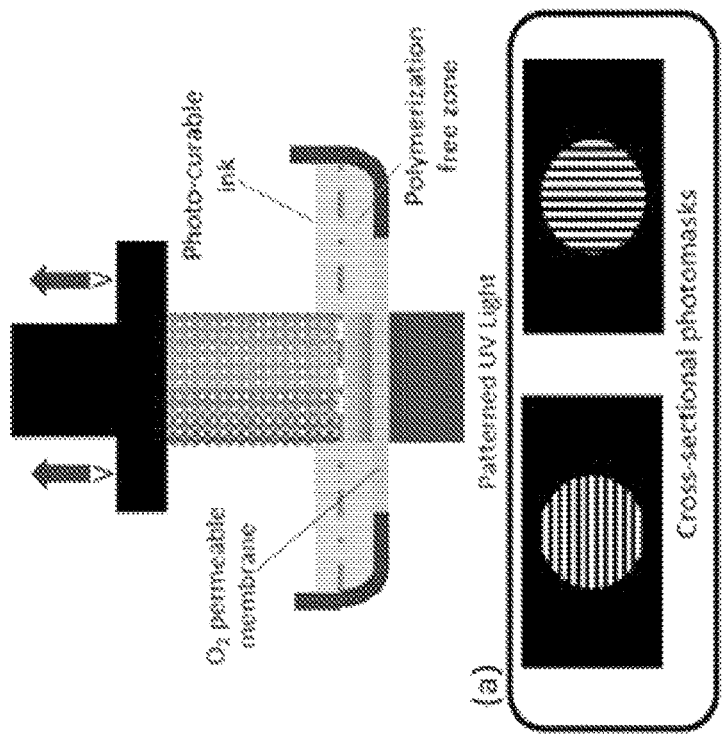
FIG. 1. (a) microCLIP 3D fabrication system schematic. (b) Top view of woodpile CAD Design (c) Top view of honeycomb cylinder design.
Figure 1:
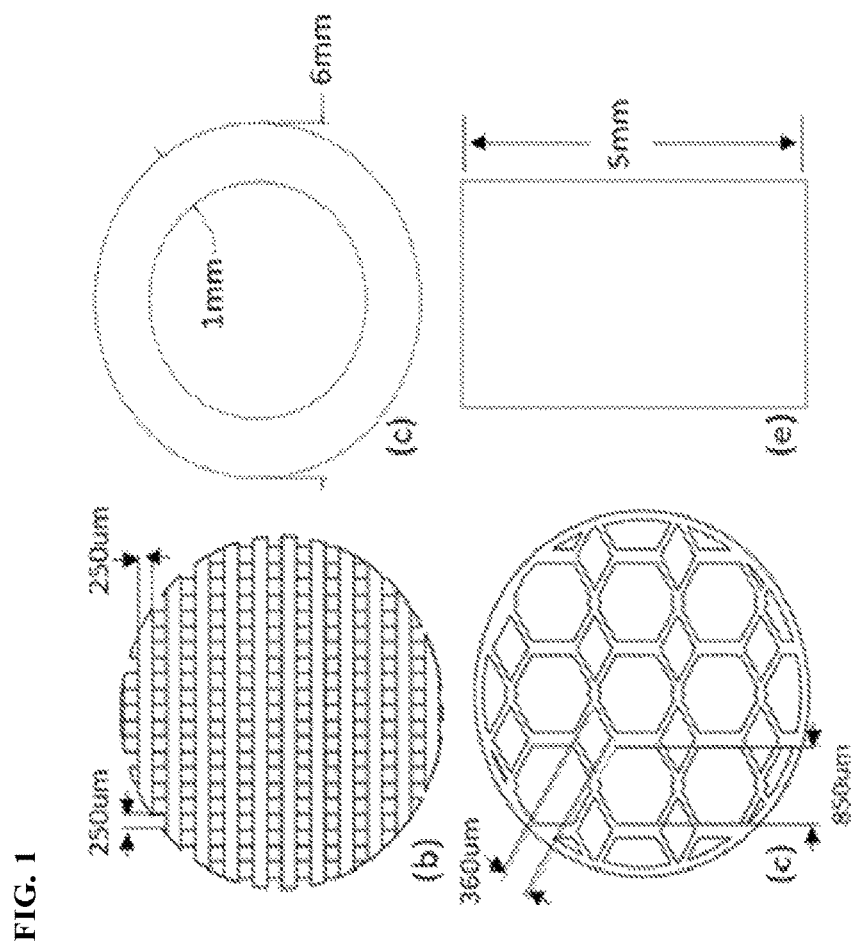

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a polymer" is a reference to one or more polymers and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about: refers to values within 10% of the recited value or range (e.g., about 50 is the equivalent of 45-55).

As used herein, the term "polymer" refers to a chain of repeating structural units or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the term "pre-polymer" refers to linear or branched polymers (e.g., not significantly crosslinked) that have the capacity to be crosslinked under appropriate conditions (e.g., to "cure" and/or form a thermoset or hydrogel), but have not been subjected to the appropriate conditions.

As used herein, the term "crosslinked polymer" refers to a polymer with a significant degree of interconnectedness between multiple polymer strands, the result of which is an insoluble polymer network. For example, multiple polymer stands may be crosslinked to each other at points within their structures, not limited to the ends of the polymer chains.

As used here, the terms "thermoset polymer" and "cured polymer" refer to a polymer network that has exhibits a sufficient degree of covalent crosslinking to render the network insoluble (e.g., in both water and organic solvents) and infusible. "Thermosetting" and/or "curing" may be achieved by thermal (e.g., heating), radiation (e.g., UV crosslinking), or chemical (e.g., chemically-induced crosslinking) means. The thermosetting/curing procedure is not reversible, except by means of chemically breaking the covalent crosslinks.

As used herein, the terms "composite" and "composite material" refer to materials or compositions generated from the combination of two or more constituent materials (e.g., compounds, polymers, etc.). The constituent materials may interact (e.g., non-covalently) at the microscopic or molecular level, but typically do not react chemically (e.g., covalently). At the macroscopic level, the constituent materials typically appear homogenous but may appear separate or distinct.

As used herein, the term "nanoparticles" refers to particles having mean dimensions (e.g., diameter, width, length, etc.) of less than 1 μm (e.g., <500 nm ("sub-500-nm nanoparticles"), <100 nm ("sub-100-nm nanoparticles"), <50 nm ("sub-50-nm nanoparticles"). Nanoparticles may be of any shape and may be two or three dimensional.

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

As used herein, the term "biostable" refers to compositions or materials that do not readily break-down or degrade in a physiological or similar aqueous environment. Conversely, the term "biodegradeable" refers herein to compositions or materials that readily decompose (e.g., depolymerize, hydrolyze, are enzymatically degraded, disassociate, etc.) in a physiological or other environment.

As used herein, the term "acrylated" refers to a compound displaying at least one moiety/substituent having the structure:

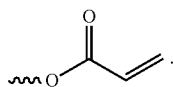

The displayed moiety is referred to as an "acrylate moiety").

As used herein, the term "methacrylteacrylated" refers to a compound displaying at least one moiety/substituent having the structure:

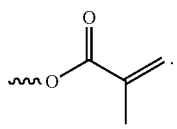

The displayed moiety is referred to as an "methacrylate moiety").

As used herein, the term "stereolithography" refers to an additive manufacturing process wherein a three-dimensional (3D) object is fabricated by depositing and hardening (e.g., polymerizing) successive layers of material in a stepwise layer-by-layer fashion. As described in U.S. Pat. No. 5,184,307, a stereolithography system will typically form a three-dimensional object in accordance with a corresponding object representation, which may be formed in a CAD system or the like. The object representation is divided into a plurality of layer representations that a stereolithography system will, in the course of building up the object in a stepwise, layer-by-layer manner, to form the physical object layers, and thus, the 3D object itself.

As used herein the term "photoinitiator" refers to a compound that undergoes a reaction (e.g., decomposition) upon absorption of light within a particular range of wavelengths, producing a reactive species (e.g., radical) that can initiate reactions (e.g., polymerization, crosslinking, etc.) of other molecules. Examples of photoinitiators include azobisisobutyronitrile (AIBN), benzoyl peroxide, 2,2-Dimethoxy-2-phenylacetophenone (DMPA), camphorquinone (CQ), phenylbis(2,4,6-trimethylbenzoyl) phosphine oxide (BAPO), 2-Hydroxy-2-methylpropiophenone (DAROCUR), ethyl 4-dimethylaminobenzoate (EDAB), and 2-Hydroxy-4'-(2-hydroxyethoxy)-2-methylpropiophenone (IRGACURE).

As used herein, the term "photopolymerization" refers to a polymerization reaction that is initiated by exposure of monomers and/or a photoinitiator to light.

As used herein, the term "photocrosslinking" refers to a crosslinking reaction that is initiated by exposure of macromolecules (e.g., polymers) and/or a photoinitiator to light.

As used herein the term "thermal initiator" refers to a compound that undergoes a reaction (e.g., decomposition) upon exposure to heat (e.g., a temperature above a particular threshold), producing reactive species (e.g., radical) that can initiate reactions (e.g., polymerization, crosslinking, etc.) of other molecules.

As used herein, the terms "thermal curing" and "thermal-induced crosslinking" refer to a curing and/or crosslinking reaction that is initiated by exposure of macromolecules (e.g., polymers) and/or a thermal initiator to heat (e.g., a temperature above a particular threshold).

As used herein, the term "malleable" refers to a material, object, device, etc. which is capable of being manipulated to some extent into a desired shape, position, and/or orientation, and which retains this manipulated shape, position, or orientation under the typical stresses and strains applied when used for an intended purpose, for example within a patient (i.e., not rigid).

As used herein, the term "rigid" refers to a material, object, device, etc. which maintains its shape, position, and/or or orientation under the typical stresses and strains applied when used for an intended purpose, for example within a patient (i.e., not malleable).

As used herein, the term "microstructure" refers to structural features, such as pores, recesses, ridges, etc., that have one or more dimensions (e.g., height, width, length, and/or diameter) that are less than 1 mm, but 1 μm or greater in length.

DETAILED DESCRIPTION

Provided herein photo-reactive inks, thermal-curable materials and objects (e.g., medical implants, scaffolds, devices, etc.) made therefrom, and methods of preparation and use thereof.

In some embodiments, objects described herein are made from a biodegradable, bioceramic-elastomer materials and/ or composites. In some embodiments, two-step methods, comprising a first photocrosslinking step and a second thermal curing step are provided. In particular embodiments, object, devices, implants, scaffolds, etc. described herein have initial elastic mechanical properties (e.g., malleable solids), which facilitates placement within a subject; however, upon implantation, due to body temperature, the material gradually hardens into a more rigid state. The compositions and methods herein find use, for example, in bone and/or soft tissue regeneration.

In some embodiments, polymers that find use as the curable component in the compositions and composites described herein display one or more reactive moieties (e.g., acrylate moiety, methacrylate moiety, etc). In some embodiments, the reactive moieties are stable in the absence of an initiator compound (e.g., diazo initiator, (e.g., V70, VA-044, etc.)). In some embodiments, the reactive moieties are stable in the absence of initiation conditions (e.g., temperatures over 25° C. (e.g., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or more), etc.).

In some embodiments, reactive polymers are acrylated polymers. In some embodiments, acrylated polymers display one or more acrylate substituents. In some embodiments, an acrylate substituent is an alkyl acrylate. Examples of alkyl acrylates include methyl acrylate, ethyl acrylate, n-propyl acrylate, isopropyl acrylate, n-butyl acrylate, sec-butyl acrylate, tert-butyl acrylate, lauryl acrylate, cyclohexyl acrylate, dicyclopentenyl acrylate and the like alone or mixtures thereof. In some embodiments, suitable polymers are acrylated by reaction between the polymer and an acrylate compound displaying a suitable moiety (e.g., epoxide moiety) for covalent attachment of the acrylate to one or more positions on the polymer. In some embodiments, glycidyl acrylate is employed to acrylate reactive positions (e.g., hydroxyl, carboxylic acids, etc.) on polymers. In some embodiments, each monomer of a polymer is acrylated. In some embodiments, each occurrence of a particular monomer in a polymer is acrylated (e.g., in a copolymer). In some embodiments, reaction of the acrylate compound (e.g., glycidyl acrylate) with a polymer is controlled (e.g., molar ratio of acrylate to polymer (e.g., 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1,100:1, or ranges therebetween), reaction conditions, reaction time, etc.) to limit the percentage of monomers and/or potentially-acrylatable monomers in a polymer that are acrylated (e.g., %, 2%, 3%, 4%, 5%, 6%, 7%, 8%, 9%, 10%, 15%, 20%, 25%, 30%, 40%, 50%, 60%, 70%, 80%, 90%, or ranges therebetween). In some embodiments, acrylated polymers crosslink and/or cure (e.g., crosslink with each other, transition from liquid and/or soluble to solid and/or insoluble) under appropriate conditions (e.g., in the presence of UV light or at a particular temperature) and in the presence of an initiator compound (e.g., photinitiator, thermal initiator, etc.).

In some embodiments, reactive polymers are methacrylated polymers. In some embodiments, methacrylated polymers display one or more methacrylate substituents. In some embodiments, a methacrylate substituent is an alkyl methacrylate. Examples of alkyl methacrylates include methyl methacrylate, ethyl methacrylate, n-propyl methacrylate, isopropyl methacrylate, n-butyl methacrylate, sec-butyl methacrylate, tert-butyl methacrylate, lauryl methacrylate, cyclohexyl methacrylate, dicyclopentenyl methacrylate and the like alone or mixtures thereof. In some embodiments, suitable polymers are methacrylated by reaction between the polymer and a methacrylate compound displaying a suitable moiety (e.g., epoxide moiety) for covalent attachment of the methacrylate to one or more positions on the polymer. In some embodiments, glycidyl methacrylate is employed to methacrylate reactive positions (e.g., hydroxyl, carboxylic acids, etc.) on polymers. In some embodiments, each monomer of a polymer is methacrylated. In some embodiments, each occurrence of a particular monomer in a polymer is methacrylated (e.g., in a copolymer). In some embodiments, reaction of the methacrylate compound (e.g., glycidyl methacrylate) with a polymer is controlled (e.g., molar ratio of acrylate to polymer (e.g., 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1,100:1, or ranges therebetween), reaction conditions, reaction time, etc.) to limit the percentage of monomers and/or potentially-methacrylatable monomers in a polymer that are methacrylated (e.g., %, 2%, 3%, 4%, 5%, 6%, 7%, 8%, 9%, 10%, 15%, 20%, 25%, 30%, 40%, 50%, 60%, 70%, 80%, 90%, or ranges therebetween). In some embodiments, methacrylated polymers crosslink and/or cure (e.g., crosslink with each other, transition from liquid and/or soluble to solid and/or insoluble) under appropriate conditions (e.g., in the presence of UV light or at a particular temperature) and in the presence of an initiator compound (e.g., photinitiator, thermal initiator, etc.).

In some embodiments, any polymer (or monomer thereof) displaying suitably reactive substituents may find use in embodiments herein. For example, any suitable polymer (or monomer thereof) may be acrylated and/or methacrylated (e.g., as described above and/or in the examples) to produce a reactive polymer that finds use in embodiments herein. For example, suitable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(hexanediol citrate), poly (octanediol citrate), poly(decanediol citrate), poly (dodecanediol citrate), etc.), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), polyethylene, acrylic resins, polyurethane, polypropylene, polymethylmethacrylate, and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). In some embodiments, any of the aforementioned polymers, when modified to display one or more reactive groups (e.g., acrylate, methacrylate, etc.), may find use at the reactive polymer component of materials described herein.

In some embodiments, reactive polymers are citric acid-based polymers. Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27 (9): p. 1889-98.; U.S. Pat. Nos. 8,772,437; 8,758,796; 8,580,912; 8,568,765; U.S. Pub. No. 2014/0155516; U.S. Pub. No. 2014/0135407; herein incorporated by reference in their entireties). Depending on the diol of choice, materials with controllable elasticity, biodegradability, and antioxidant properties can be developed (Serrano et al. Adv Mater, 2011. 23 (19): p. 2211-5.; Yang J., et al., A thermoresponsive biodegradable polymer with intrinsic antioxidant properties. Biomacromolecules, 2014. 15 (11): 3942-52.; U.S. Pub. No. 2014/0037588; herein incorporated by reference in its entirety). In some embodiments, polydiolcitrates comprise alternating diol (e.g., linear aliphatic diols) and citrate monomers. In some embodiments, the diol is between 2 and 30 carbons in length (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or ranges therebetween (e.g., 6-16, 7-14, etc.)). In some embodiments, a linear aliphatic diol is X carbons in length and comprises OH substituents at the 1 and X positions (e.g., 1,4-butanediol, 1,6-hexanediol, 1,8-octanediol, 1,10-decanediol, 1,12-dodecanediol, or any terminally-OH-substituted linear aliphatic diol from about 2-20 carbons in length). In certain embodiments, the diol comprises one or more C2-C20 alkyl-diols, C2-C20 alkenyl-diols, or mixtures thereof. In certain other embodiments, the diol comprises one or more C2-C20 alkyl-diols, such as a C6-C20 alkyl-diol, or a C6-C14 alkyl-diol, or a C6-C12 alkyl-diol. For example, the diol comprises an alkanediol, such as 1,12-dodecanediol, 1,10-decanediol, 1,8-octanediol, or a mixture thereof. In another example, the diol comprises 1,10-decanediol, 1,8-octanediol, or a mixture thereof. In another example, the diol comprises 1,8-octanediol (e.g., the polyester is poly(1,8-octanediol-citrate).

In some embodiments, reagents, monomer components of polymers, methods, reaction conditions, etc. that find use in embodiments described herein are described in: U.S. Pat. Nos. 8,911,720; 8,772,437; 8,758,796; 8,580,912; 8,568,765; 8,404,264; U.S. Pub. No. 2014/0058049; U.S. Pub. No. 2013/0211500; U.S. Prov. App. No. 62/160,334; herein incorporated by reference in their entireties.

In some embodiments, materials comprise a poly(glycerol-diacid). A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid) s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), C2-C20 alkyl-diacids, C2-C20 alkenyl-diacids, and mixtures thereof.

In some embodiments, polymers are selected having reactive side groups that facilitate crosslinking and/or curing of the polymers, induced by an initiator (e.g., photoinitiator, thermal initiator) and initiation conditions (e.g., light (e.g., visible, UV, etc.), heat (e.g., physiologic temperature), etc.). In other embodiments, polymers (e.g., selected for their physical/mechanical characteristics) are modified to display reactive groups (e.g., acrylates, methacrylates, etc.). For example, in some embodiments, acrylate and/or methacrylate groups are added to polymers by reacting the polymers with a glycidyl methacrylate compound, glycidyl acrylate, or other acrylate/methacrylate-displaying reactive compounds. In some embodiments, methacrylated poly(diol citrates) are synthesized using methods and reagents understood in the field and/or described in the literature, for example, Wang et al. (Biomater Sci. 2013 June; 1 (6): 625-632.; incorporated by reference in its entirety). In particular embodiments, poly(diol citrate) pre-polymer is methacrylated by dissolving the prepolymer in tetrahydrofuran, adding imidazole and then glycidyl methacrylate. The mixture is stirred under heat (e.g., about 60° C.). Solvent is removed (e.g., by rotary evaporation). The resulting methacrylated poly(diol citrate) may be purified in Milli-Q water and lyophilized to dryness. Acrylated poly(diol citrates) (aP(DC)s) are synthesized using analogous methods and reagents. Related polymers (e.g., comprising additional monomers and/or substituents) are acrylated/methacrylated using similar methods that are understood in the field and/or in references incorporated herein. Other polymers that find use in embodiments herein are acrylated/methacrylated using available methods. Other reactive groups may be added to polymers (e.g., poly(diol citrate) s or other polymers) using available chemistries and the disclosure herein.

In some embodiments, materials and methods herein comprise photoinitiators that induce polymerization and/or crosslinking of the reactive polymers and/or monomers described herein (e.g., displaying reactive moieties (e.g., acrylate and/or methacrylate moieties), etc.). In some embodiments, photoinitiators are small molecules that produce free radicals, cations, or anions when exposed to light of an appropriate wavelength (UV light (e.g., 10-400 nm (e.g., 10 nm, 20 nm, 40 nm, 60 nm, 80 nm, 100 nm, 120 nm, 140 nm, 160 nm, 180 nm, 200 nm, 220 nm, 240 nm, 260 nm, 280 nm, 300 nm, 320 nm, 340 nm, 360 nm, 380 nm, 400 nm, or ranges therebetween))). The free radicals, cations, or anions then initiate crosslinking and/or polymerization of reactive moieties displayed on the monomers or polymers. In some embodiments, a thermal initiator is water soluble, oil soluble, soluble is organic solvent, etc.

In some embodiments, a photoinitiator is a free-radical photoinitiator, a cationic photoinitiator, or an anionic photoinitiator. Classes of photoinitiators include, but are not limited to: benzoin ethers, benzyl ketals, α-dialkoxy acetophenones, α-hydroxy alkylphenomes, α-amino alkylphenomes, acylphosphine oxides, benzophenomes/benzoamines, thioxanthones/thioamines, etc. Examples of photoinitiators include, but are not limited to: acetophenone, anisoin, anthraquinone, anthraquinone-2-sulfonic acid monohydrate, (benzene) tricarbonylchromium, benzil, benzoin, benzoin ethyl ether, benzoin isobutyl ether, benzoin methyl ether, benzophenone, benzophenone/1-hydroxycyclohexyl phenyl ketone (blend), 3,3',4,4'-benzophenonetetracarboxylic dianhydride, 4-benzoylbiphenyl, 2-benzyl-2-(dimethylamino)-4'-morpholinobutyrophenone, 4,4'-bis (diethylamino) benzophenone, 4,4'-bis(dimethylamino) benzophenone, camphorquinone, 2-chlorothioxanthen-9-one, (cumene) cyclopentadienyliron (ii) hexafluorophosphate, dibenzosuberenone, 2,2-diethoxyacetophenone, 4,4'-dihydroxybenzophenone, 2,2-dimethoxy-2-phenylacetophenone, 4-(dimethylamino) benzophenone, 4,4'-dimethylbenzil, 2,5-dimethylbenzophenone, 3,4-dimethylbenzophenone, diphenyl(2,4,6-trimethylbenzoyl) phosphine oxide/2-hydroxy-2-methylpropiophenone (blend), 4'-ethoxyacetophenone, 2-ethylanthraquinone, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, thioxanthen-9-one, triarylsulfonium hexafluoroantimonate salts, triarylsulfonium hexafluorophosphate salts, etc.

In some embodiments, a photoinitiator is selected based upon the half-life of the photoinitiator when exposed to the appropriate wavelength of light. In some embodiments, the half-life of the photoinitiator determines the rate at which reactive species (e.g., cations, anions, radicals, etc.) are produced. In some embodiments, a polymerization and/or crosslinking step (e.g., a stereolithography step), facilitated by the photoinitiator, is a fast step (e.g., on the time scale of seconds or minutes). In some embodiments, the half-life of a suitable photoinitiator when exposed to the appropriate wavelength of light is between 1 second and 10 minutes (e.g., 1 second, 2 seconds, 5 seconds, 10 seconds, 20 seconds, 30 seconds, 45 seconds, 1 minute, 2 minutes, 3 minutes, 4 minutes, 5 minutes, 6 minutes, 7 minutes, 8 minutes, 9 minutes, 10 minutes, or ranges therebetween (e.g., 1-10 seconds)). In some embodiments, a photoinitiator is selected based on the reactivity of its decomposition product (e.g., free radical, cation, anion, etc.) with the reactive groups of the monomers and/or polymers to be polymerized and/or crosslinked.

In some embodiments, materials and methods herein comprise thermal initiators that induce curing of the reactive polymers described herein (e.g., displaying reactive moieties (e.g., acrylate and/or methacrylate moieties), etc.). In some embodiments, thermal initiators are small molecules that produce free radicals, cations, or anions when exposed to heat (e.g., temperatures above a threshold (e.g., 34° C., 35° C., 36° C., 37° C., 38° C., 39° C., 40° C., or ranges therebetween). The free radicals, cations, or anions then initiate crosslinking of reactive moieties displayed on the polymers. In some embodiments, activation of thermal initiators (e.g., by heat) results in curing of a reactive material (e.g., displaying reactive moieties (e.g., acrylate and/or methacrylate moieties), etc.). In some embodiments, curing occurs over a time span (e.g., 1 minute, 2 minutes, 5 minutes, 10 minutes, 20 minutes, 30 minutes, 1 hour, 2 hours, 4 hours, or more, or ranges therebetween). In some embodiments, the curing results in the formation of a thermoset material. In some embodiments, a thermal initiator is water soluble, oil soluble, soluble is organic solvent, etc. In some embodiments a thermal initiator is an azo-initiator. Suitable azo initiators are available, for example, from Wako Specialty Chemicals, and include for example:

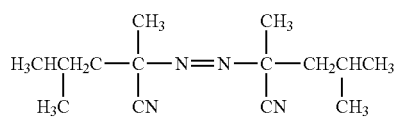

V-65

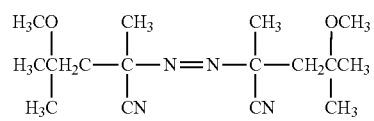

V-70

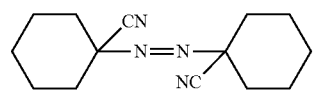

V-40

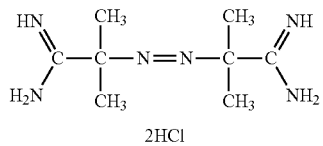

V-50

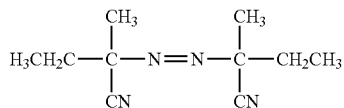

V-59

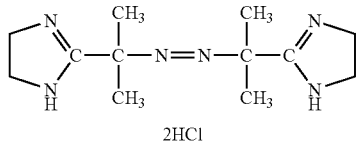

VA-044

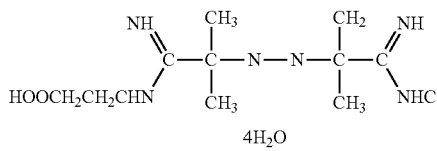

VA-057

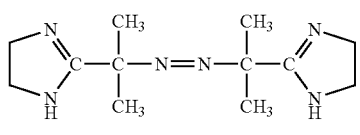

VA-061

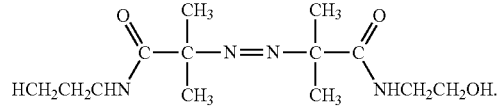

VA-086

Other examples of suitable initiators include azo-N,N'-bisdimethylvaleronitrile (ABDV), azo-N,N'-bisisobutyronitrile (AIBN), or any other azo-based initiator. In some embodiments, other initiators, such as, peroxides, halogens, metal iodides, metal alkyls, persulfates, etc. find use in embodiments herein as thermal initiators, to the extent that they initiate curing of reactive polymers under desired temperature conditions.

In some embodiments, a thermal initiator is a free-radical thermal initiator. Examples of free-radical thermal initiators include: tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy) butane, 1,1-bis(tert-butylperoxy) cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, potassium persulfate, etc.

In some embodiments, a thermal initiator is a cationic thermal initiator. Examples of cationic thermal initiators include: dicyandiamide, cyclohexyl p-toluenesulfonate, diphenyl(methyl) sulfonium tetrafluoroborate, etc.

In some embodiments, a thermal initiator is a anionic thermal initiator. Examples of anionic thermal initiators include: phosphonamidates, hydroxylamide, etc.

In some embodiments, a thermal initiator is selected based upon the half-life of the thermal initiator at a desired temperature. In some embodiments, the half-life of the thermal initiator determines the rate at which reactive species (e.g., cations, anions, radicals, etc.) are produced. In some embodiments, a curing step, facilitated by the thermal initiator, is a slow step (e.g., on the time scale or minutes, 10s of minutes, or hours). In some embodiments, the half-life of a suitable thermal initiator at a desired temperature (e.g., physiologic temperature) is between 1 minute and 10 hours (e.g., 1 minute, 2 minutes, 5 minutes, 10 minutes, 20 minutes, 30 minutes, 45 minutes, 1 hour, 2 hours, 3 hours, 4 hours, 5 hours, 6 hours, 7 hours, 8 hours, 9 hours, 10 hours, or ranges therebetween). In some embodiments, a thermal initiator is selected based on the reactivity of its decomposition product (e.g., free radical, cation, anion, etc.) with the reactive groups of the polymers to be cured.

In some embodiments, composite materials herein or reactants for synthesizing composite materials herein comprise 0.1%-10% (e.g., 0.1%, 0.2%, 0.5%, 0.75%, 1%, 1.25%, 1.5%, 1.75%, 2%, 2.5%, 3%, 4%, 5%, 6%, 7%, 8%, 9%, 10%, or ranges therebetween) thermal initiator (e.g., V70, IRGACURE, other thermal initiators herein, or combinations thereof).

In some embodiments, materials described herein comprise composites of the reactive polymer materials described herein and one or more additional components (e.g. in additional to initiator compounds). In some embodiments, additional components comprise 1-99 wt % of the composite material (e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or ranges therebetween).

In some embodiments, a composite material comprises at least 1% (e.g., >>1%, >2%, >3%, >4%, >5%, >10%, >20%, >30%, >40%, >50%, >60%, >70%, >80%, >90%, >95%, >98%, >99%) reactive polymer (e.g., citrate-based polymer (e.g., methacrylated poly(diol citrate), etc.)). In some embodiments, a composite material comprises less than 99% (e.g., <99%, <98%, <95%, <90%, <80%, <70%, <60%, <50%, <40%, <30%, <20%, <10%, <5%, <4%, <3%, <2%, <1%) reactive polymer (e.g., citrate-based polymer (e.g., methacrylated poly(diol citrate), etc.)). In some embodiments, a composite material comprises reactive polymer (e.g., citrate-based polymer (e.g., methacrylated poly(diol citrate), etc.)) in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, or ranges therebetween. In some embodiments, a composite material comprises 1-99% (e.g., 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or ranges therebetween) reactive polymer (e.g., citrate-based polymer (e.g., methacrylated poly(diol citrate), etc.)). The aforementioned percentages may be wt % or molar %.

In some embodiments, provided herein is a mixture comprising: (1) a citrate-based polymer component (e.g., methacrylated poly(diol citrate), etc.), (2) a photoinitiator, (3) an thermal initiator (e.g., V70, VA-044, etc.), and (4) an additional structural component (e.g., bioceramic, polymer, etc.). In some embodiments, the mixture further comprises a solvent and/or additional components. In some embodiments, exposure of such a mixture to the appropriate wavelengths of light (e.g., via light-induced 3D printing system) results in formation of a composite material comprising: (1) a photocrosslinked-version of the citrate-based polymer component (e.g., methacrylated poly(diol citrate), etc.), (2) the thermal initiator (e.g., V70, VA-044, etc.), and (3) the additional structural component (e.g., bioceramic, polymer, etc.).

In some embodiments, the mixture further comprises a suitable solvent (e.g., for dissolving one or more reagents in). In some embodiments, suitable solvents may be selected from: MeOH, EtOH, dioxane, acetone, 1,3-dioxlane, N,N-dimethylformamide, etc. In some embodiments, solvents are included in a reagent mixture at a wt % or molar % of between 5% and 50% (e.g., 5%, 10%, 15%, 20%, 25%, 30%, 35%, 40%, 45%, 50%, or ranges therebetween).

In some embodiments, provided herein are composite materials (e.g., malleable solid materials) comprising: (1) a photocrosslinked citrate-based polymer component (e.g., methacrylated poly(diol citrate), etc.), (2) an thermal initiator (e.g., V70, VA-044, etc.), and (3) an additional structural component (e.g., bioceramic, polymer, etc.). In some embodiments, exposure of such a compound to the appropriate temperature (e.g., by placing the material into a physiologic system (e.g., implanting in a subject)) results in formation of a rigid material comprising: (1) a photo/thermal crosslinked-version of the citrate-based polymer component (e.g., methacrylated poly(diol citrate), etc.) and (2) the additional structural component (e.g., bioceramic, polymer, etc.).

In particular embodiments, composites of reactive citrate-based polymer materials and a bioceramic component are provided. Suitable bioceramics include hydroxyapatite (HA; $Ca_{10}(PO_4)_6(OH)_2$), tricalcium phosphate beta (β TCP; $Ca_3(PO_4)_2$), and mixtures of HAP and β TCP. In some embodiments, bioceramic nanoparticles and/or bioceramic microparticles find use in embodiments herein and/or are a component of a composite material within the scope herein. In some embodiments, bioceramics (e.g., TCP) are provided as nanoparticles or microparticles. In some embodiments, bioceramic particles within the materials and mixtures herein comprise mean diameters of 50 nm to 10 μm (e.g., 50 nm, 75 nm, 100 nm, 150 nm, 200 nm, 250 nm, 300 nm, 400 nm, 500 nm 750 nm, 1 μm, 2 μm, 3 μm, 4 μm, 5 μm, 6 μm, 8 μm, 10 μm, or ranges therebetween (e.g., 150 nm to 5 μm).

In some embodiments, other additives are included in the composites of reactive citrate-based polymer materials described herein. For example, in some embodiments a metal organic frameworks (MOFs), such as copper (Cu) MOFs are included in composites herein and/or mixtures for the synthesis thereof. The inclusion of MOFs in polymer composites is described, for example in U.S. Pub No. 2018/0236122, POLYMER METAL-ORGANIC FRAMEWORK COMPOSITES; herein incorporated by reference in its entirety). In some embodiments, the MOF comprises transition metal nodes connected by a organic ligands. In some embodiments, the transition metal is selected from the list consisting of: copper (Cu), zinc (Zn), magnesium (Mg), cobalt (co), Nickel, (Ni), iron (Fe), manganese (Mn), palladium (Pd), chromium (Cr), lead (Pb), titanium (Ti), and combinations thereof. In some embodiments, the transition metal is copper. In some embodiments, the organic ligand comprises: (a) a substructure comprising alkyl, cycloalkyl, heteroalkyl, aryl, and heteroaryl groups; the substructure displaying (b) a plurality of metal ion coordination groups. In some embodiments, the metal ion coordination groups comprise COOH groups. In some embodiments, the organic ligand comprises a molecule selected from the list consisting of: 1,4-di(4'-pyrazolyl) benzene, 1,4,7,10-tetraazacyclodo-decane-n,n',n'',n'''-tetraacetic acid, 2,4,6-(tri-4-pyridinyl)-1,3,5-triazine, tris(isobutylaminoethyl) amine, [1,1'-biphenyl]-4,4'-dicarboxylic acid, 2,5-dihydroxyterephthalic acid, 2,6-naphthalenedicarboxylic acid, 1,4-phenylenediacetic acid, 1,1,2,2-tetra(4-carboxylphenyl) ethylene, 1,3,5-tricarboxybenzene, 1,3,5-tris(4-carboxyphenyl) benzene, and 2-(diphenylphosphino) terephthalic acid. In some embodiments, the MOF comprises copper metal ion nodes linked by 1,3,5-tricarboxybenzene organic ligands. In some embodiments, a MOF (e.g., Cu MOF) is included in a composited herein or a reaction mixture to produce such a composite in a wt % or molar % of 0.1%-10% (e.g., 0.1%, 0.2%, 0.5%, 0.75%, 1%, 1.25%, 1.5%, 1.75%, 2%, 2.5%, 3%, 4%, 5%, 6%, 7%, 8%, 9%, 10%, or ranges therebetween).

In some embodiments, provided herein is a mixture comprising: (1) a citrate-based polymer component (e.g., methacrylated poly(diol citrate), etc.), (2) a photoinitiator, (3) an thermal initiator (e.g., V70, VA-044, etc.), and (4) a bioceramic component (e.g., bioceramic nanoparticles and/or bioceramic microparticles). In some embodiments, the mixture further comprises a solvent and additional components. In some embodiments, exposure of such a mixture to the appropriate wavelengths of light (e.g., via light-induced 3D printing system) results in formation of a composite material comprising: (1) a photocrosslinked-version of the citrate-based polymer component (e.g., methacrylated poly (diol citrate), etc.), (2) the thermal initiator (e.g., V70, VA-044, etc.), and (3) the bioceramic component (e.g., bioceramic nanoparticles and/or bioceramic microparticles).

In some embodiments, provided herein are composite materials (e.g., malleable solid materials) comprising: (1) a photocrosslinked citrate-based polymer component (e.g., methacrylated poly(diol citrate), etc.), (2) an thermal initiator (e.g., V70, VA-044, etc.), and (3) a bioceramic component (e.g., bioceramic nanoparticles and/or bioceramic microparticles). In some embodiments, exposure of such a compound to the appropriate temperature (e.g., by placing the material into a physiologic system (e.g, implanting in a subject)) results in formation of a rigid material comprising: (1) a photo/thermal crosslinked-version of the citrate-based polymer component (e.g., methacrylated poly(diol citrate), etc.) and (2) the bioceramic component (e.g., bioceramic nanoparticles and/or bioceramic microparticles).

In some embodiments, the bioceramic component comprises 1-99 wt % of the composite material (e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or ranges therebetween (e.g., 5-65 wt %, 10-60 wt %, 20-50 wt %, etc.). In some embodiments, the bioceramic (e.g., HA, β TCP, etc.) component comprises bioceramic nanoparticles. In some embodiments, the mean diameter of nanoparticles used in embodiments herein is less than 1 μm (e.g., 900 nm, 800 nm, 700 nm, 600 nm, 500 nm, 400 nm, 300 nm, 250 nm, 200 nm, 150 nm, 100 nm, 75 nm, 50 nm, 25 nm, 20 nm, 15 nm, 10 nm, or less, or ranges therebetween).

In some embodiments, composite materials comprise one or more additional polymeric components (e.g., in addition to the citrate-based polymer component (e.g., methacrylated poly(diol citrate)). Suitable biodegradable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly (hydroxyl acids), poly(L-lactide) poly(D,L lactide), poly(D, L-lactide-co-glycolide), poly(L-lactide-co-glycolide), copolymers of lactic acid and glycolic acid, copolymers of ε-caprolactone and lactide, copolymers of glycolide and s-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). Suitable non-biodegradable polymers include silicone rubber, polyethylene, acrylic resins, polyurethane, polypropylene, and polymethylmethacrylate.

In some embodiments, polymers are obtained and/or prepared according to standard techniques. For example, methods and materials for synthesis of poly(diol citrate) polymers and related polymers (e.g., further comprising glycerol or other additional monomers) are described in the literature, such as Yang et al. (Biomaterials. 2006 March; 27 (9): 1889-98.; incorporated by reference in its entirety) and other patents and publications incorporated herein by reference in their entireties. In some embodiments, to synthesize poly(diol citrate) polymer, approximately equimolar amounts of citric acid and diol (e.g., linear aliphatic diol, terminal-OH diols, one diol species, multiple diol species, etc.) are melted together (e.g., under inert (e.g., nitrogen) atmosphere, at about 165° C., etc.) with stirring (e.g., for 20 min). The temperature is subsequently decreased to an appropriate polymerization temperature (e.g., about 140° C.) and the mixture is stirred (e.g., for 30-120 min) to obtain the poly(diol citrate) pre-polymer. In some embodiments, the pre-polymer is dissolved in ethanol, purified in Milli-Q water, and/or lyophilized to dryness. Related polymers (e.g., comprising additional monomers and/or substituents) are prepared using similar methods that are understood in the field and/or in references incorporated herein. Other polymers that find use in embodiments herein are obtained and/or prepared using available methods and the disclosure herein.

In some embodiments, provided herein is a mixture comprising: (1) a citrate-based polymer component (e.g., methacrylated poly(diol citrate), etc.), (2) a photoinitiator, (3) an thermal initiator (e.g., V70, VA-044, etc.), and (4) a polymeric component (e.g., comprising a bioactive moiety). In some embodiments, the mixture further comprises a solvent and/or additional components. In some embodiments, exposure of such a mixture to the appropriate wavelengths of light (e.g., via light-induced 3D printing system) results in formation of a composite material comprising: (1) a photocrosslinked-version of the citrate-based polymer component (e.g., methacrylated poly(diol citrate), etc.), (2) the thermal initiator (e.g., V70, VA-044, etc.), and (3) the polymeric component (e.g., comprising a bioactive moiety).

In some embodiments, provided herein are composite materials (e.g., malleable solid materials) comprising: (1) a photocrosslinked citrate-based polymer component (e.g., methacrylated poly(diol citrate), etc.), (2) an thermal initiator (e.g., V70, VA-044, etc.), and (3) a polymeric component (e.g., comprising a bioactive moiety). In some embodiments, exposure of such a compound to the appropriate temperature (e.g., by placing the material into a physiologic system (e.g., implanting in a subject)) results in formation of a rigid material comprising: (1) a photo/thermal crosslinked-version of the citrate-based polymer component (e.g., methacrylated poly(diol citrate), etc.) and (2) the polymeric component (e.g., comprising a bioactive moiety).

In some embodiments, compositions and methods are provided that utilize a two-step procedure for (1) forming 3D structures from desired materials, and (2) curing the 3D structures into a fixed position/shape/orientation.

In some embodiments, the first step is a polymerization (of reactive monomers) or crosslinking (of reactive polymers) reaction that is facilitated by the presence of a photoinitiator. In some embodiments, the photoinitiator allows for stereolithographic methods (e.g., photo-induced 3D printing) to be used to fabricate a 3D object or device from a desired polymeric material. In some embodiments, the photoinitiator initiates a rapid polymerization/crosslinking reaction to facilitate the repeated reactions required for stereolithography (e.g., 3D priniting). In some embodiments, the photoinitiator-induced reaction results in a solid material, but one that exhibits a degree of malleability (e.g., not completely rigid, not a thermoset, incomplete crosslinking of reactive groups, etc.).

Any suitable 3D printing and/or additive manufacturing techniques and/or systems that make use of photo-induced polymerization may find use in embodiments herein. For example, in conventional additive or three-dimensional fabrication techniques, construction of a three-dimensional object is performed in a step-wise or layer-by-layer manner. In particular, layer formation is performed through solidification of photo-curable resin under the action of visible or UV light irradiation. Layers may be formed on the top or bottom surface of a growing object (e.g., U.S. Pat. No. 5,236,637; incorporated by reference in its entirety). Many 3D printing techniques are understood in the file and applicable to embodiments herein. Alternatively, methods of continuous liquid interface printing (or processing) CLIP are provided (e.g., U.S. Pat. No. 9,360,757; incorporated by reference in its entirety). CLIP uses photo polymerization to create objects of a wide variety of shapes. The continuous process begins with a pool of liquid photopolymer resin. Part of the pool bottom is transparent to ultraviolet light (the "window"). An ultraviolet light beam shines through the window, illuminating the precise cross-section of the object. The light causes the resin to solidify. The object rises slowly, to allow resin to flow under and maintain contact with the bottom of the object. An oxygen-permeable membrane lies below the resin, which creates a persistent liquid interface that prevents the resin from attaching to the window and prevents photopolymerization between the window and the polymerizer.

In some embodiments, techniques and systems are selected (e.g., microCLIP) that allow for the fabrication of objects displaying microscale features (microstructures), such as pores. In some embodiments, techniques are utilized that, using the materials described herein, are useful in producing objects of any suitable shape with feature resolution of as low as 10 μm (e.g., 10 μm resolution, 15 μm resolution, 20 μm resolution, 25 μm resolution, 30 μm resolution, 35 μm resolution, 40 μm resolution, 45 μm resolution, 50 μm resolution, etc.).

In some embodiments, the second step is a curing reaction (e.g., extensive crosslinking between reactive groups) that is facilitated by the presence of a thermal initiator. In some embodiments, the thermal initiator allows for fixing a 3D object or device into a desired shape/position/orientation. In some embodiments, the first step produces a solid object of defined shape and optionally comprising desired microstructures, but the object is soft or malleable. In some embodiments, the shape of the first-step object can be manipulated by a user, for example, when inserting the object into a location for a desired application (e.g., into a subject). In some embodiments, the dimensions of the first-step object can be altered by up to 25% (e.g., 1%, 2%, 5%, 10%, 15%, 20%, 25%, or ranges therebetween) due to the malleability of the object. In some embodiments, the thermal initiator initiates a slow curing reaction allows the object/device to be manipulated into a desired shape/position/orientation (e.g., implanted into a subject) as it becomes a more rigid material. In some embodiments, the thermal-initiator-induced reaction results in a rigid material (e.g., thermoset) that will maintain its shape/position/orientation under forces/stresses consistent with the particular use. In some embodiments, the second step curing results in near complete (e.g., >90%, >95%, >99%, etc.) crosslinking of reactive groups and formation of a thermoset.

As described throughout, provided herein are materials (e.g., inks) that are photo-crosslinkable to form thermo-responsive materials (e.g., polymers and composites thereof) and objects (e.g., biocompatible devices) made therefrom. The two-step fabrication process allows: (1) an object of a desired size, shape, microstructure (e.g., porosity (e.g., pore size and density)) to be fabricated using photo-induced printing techniques (e.g., microCLIP), (2) the object to be placed in a desired location and conformation for a desired application, and (3) the object to be fixed (e.g., cured) into the desired location and conformation by the application of heat to the object (e.g., from the physiologic location of the object, externally-applied heat, etc.).

These materials find use in a variety of applications. For example, materials herein find use in any application an object (e.g., of desired shape/size/microstructure) is applied in a malleable form, and then is rendered rigid when exposed to heat (e.g., physiological temperature). Materials described herein find use, for example, in medical and dental bone repair applications, such as, repair of craniofacial injuries, stabilizing complex fractures, promoting bone growth, bone regeneration, as a bone-void filler, adhering implants, etc. In some embodiments, materials find use in soft tissue repair. In some embodiments, materials find use in scaffolds for cell or tissue transplantation. In some embodiments, material find use in medical implants, such as stents, valves, etc. In some embodiments, materials find use in non-medical/dental applications.

In some embodiments in which the materials herein are used for the repair, stabilization, regeneration, growth, etc. of bone or bone fractures/injuries, the materials further comprise additional components/agents to facilitate incorporation into bone, bone growth, bone regeneration, etc. In some embodiments, additional components/agents are incorporated into the materials and encapsulated within the material upon first-step crosslinking. In such embodiments, additional components/agents are non-covalently associated with the polymer and other components of the materials. In other embodiments, additional components/agents are covalently-linked to the reactive polymer and/or other components (e.g., bioceramic) of the material.

In some embodiments, the materials described herein find use in the delivery of growth factors or other bioactive agents for the repair of bone defects and/or regeneration of bone. Suitable agents for use in embodiments herein include bone morphogenic proteins (e.g., BMP-1, BMP-2, BMP-4, BMP-6, and BMP-7); members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); vascular endothelial growth factor (VEGF); fibroblast growth factor (FGF); etc. These agent, or others, may be covalently linked to materials described herein or components thereof, non-covalently associated with moieties displayed on materials described herein or components thereof, embedded within materials described herein, etc.

EXPERIMENTAL

Example 1

Methods
Bone Scaffold and Polydiol Citrate Inks

The primary pre-polymer utilized for 4D fabrication of bone scaffolds is a biodegradable bioceramic-polyester composite. Polyester binder matrix material within the composite ink is an elastomeric citric-acid-based biomaterial (CBB) known as methacrylated poly(1,8-octanediol-citrate) (mPOC) and the bioactive ceramic hydroxyapatite (HA). Synthesis of mPOC prepolymer is described in Ref. 8 (incorporated by reference in its entirety) and the composite pre-polymer are combined as described in Refs. 4 & 17 (incorporated by reference in their entireties). Hydroxyapatite nanopowder (~500 nm) was purchased from Sigma. Methacrylated POC/HA mixture had a ratio of 40/60. Methacrylated POC/HA mixture was considered one component of the microCLIP printer ink. Methacrylated POC/HA mixture, as prepared, possessed a clay-like consistency, which required a solvent to reduce viscosity. Bone Scaffold fabrication ink contained 70 wt. % POC/HA mixture, 2.2 wt. % Irgacure 819 (BAPO photoinitiator), 3% ethyl 4 dimethylamino benzoate (EDAB, an amine synergist co-photoinitiator), and 24.8 wt. % ethanol. Other methacrylated poly(diol citrate) inks utilized for multimaterial prints and heat-assisted polymerization tests. Soft tissue scaffold ink used in multimaterial prints contained 60 wt. % mPDC, 2.2 wt. % Irgacure 819, 3 wt. % EDAB, 0.1 wt. % Tinuvin 171 (UV absorber), and 34.7 wt % ethanol. Heat-Assisted Polymerization Ink consisted of 69.83 wt. % mPOC, 1 wt. % Irgacure 819, 1 wt. % V-70 (heat induced radical initiator), 3 wt. % EDAB, and 25.17 wt. % ethanol. Inks were sonicated for 1 hour to ensure powders were well incorporated, with exception of Heat-Assisted Polymerization ink.

MicroCLIP (3D Printing of Scaffolds)

3D fabrication of parts was performed using a custom-made microCLIP device. The microCLIP device utilizes 365 nm wavelength UV light for photopolymerization. The system's dynamic mask generator is a 1080p digital micro-mirror device. Pixel resolution at the focal plane is 7.1 um×7.1 um. Printed designs were sliced with a layer thickness of 5 um. Maximum power at the focal plane of the system is approximately 6.01 mW and power density of 17.055 mW/cm².

Designs Utilized

Bone scaffolds that were initially printed utilized a simple wood pile design (FIG. 1(b)). Pores in the wood pile design were given a width of 250 um that are interconnected within the volume. Simple tubes with 6 mm OD, wall thickness of 1 mm, and height of 5 mm were fabricated for the UV and heat induced polymerization experiments. Single cross-section honeycomb cylinders consisting of internal hexagonal and diamond shaped pores were fabricated for the multimaterial printing example (FIG. 1(c)). Thicknesses of outer wall and internal hexagon/diamonds also had 150 and 200 um thicknesses.

Light and Heat Activated Polymerization (4D)

Investigation into 4D capability was performed using the mPOC matrix material, as the mPOC component is the photopolymerizable element in the ink. The mPOC ink contained 69.83 wt. % mPOC, 1 wt. % Irgacure 819, 1 wt. % V-70, 3 wt. % EDAB, and 25.17 wt. % ethanol. V-70 (2,2'-azobis(4-methoxy-2,4-dimethylvalerontirile)) is a heat induced radical initiator. V-70 was selected as it has a 10-hour half-life decomposition temperature at 30° C. (Ref. 16; incorporated by reference in its entirety). Tubes fabricated with this ink were placed into an oven at 37° C. to determine the effects human body temperature has on mechanical properties. Tubes were exposed to human body temperature for 0, 0.5, and 6.25 hours.

Mechanical Testing

Compression tests on the rings were performed via an Instron 5544 mechanical testing apparatus at a compression rate of 1 mm mm⁻¹.

Morphology

Morphology of the printed composite ink was observed via a NOVA600 SEM.

Results
Intensity/Speed Calibration

In order to 3D print with the composite material, the photo-curing characteristics of the ink were determined. In typical curing depth tests, intensity of the light is varied, while the exposure time is held constant. The model of curing depth of the material is based on the following equation:

$$C_D = D_P * \ln\left(\frac{E_{max}}{E_c}\right), \quad (1)$$

$$E_{max} = P_f * t_{exp} \quad (2)$$

where $D_P$ (penetration depth) is the slope of the semi-log plot of the $C_D$ vs. $E_{max}$ (also known as the stereolithography working curve) and $E_C$ being the critical amount of energy flux necessary to begin photopolymerization (Ref. 18; incorporated by reference in its entirety). $E_C$ is the X-axis intercept point of the working curve. $E_{max}$, or maximum energy flux, is determined by the intensity or power density ($P_f$) at the focal plane multiplied by the exposure time ($t_{exp}$). In the working curve, $E_{max}$ is plotted in the logarithmic scale. Because microCLIP involves movement of the stage during curing, it was necessary to determine a calibration method that could be run as a standard print. In addition, the curing depth equation (1) can be changed to include velocity terms with a few assumptions:

$$t_{exp} = \frac{X}{v_s} \quad (3)$$

$$v_c = \frac{P_f * X}{E_c} \quad (4)$$

$$C_D = D_P * \ln\left(\frac{v_c}{v_s}\right) \quad (5)$$

General Form: $C_D = b - D_P * \ln(v_s)$ where X is the layer slice thickness, $v_s$ is the substrate vertical speed, and $v_e$ is the critical maximum velocity that polymerization can occur.

Figure 2:
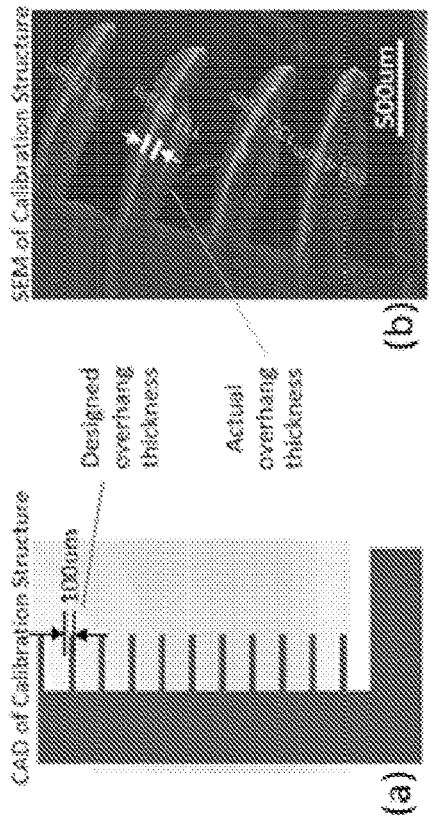
FIG. 2. (a) CAD model of calibration structure. (b) SEM of fabricated calibration structure. (c) Experimentally determined Speed Working Curve for the Bone Scaffold Ink at 35% of maximum intensity (1.15 mW/cm$^2$) at the focal plane.
Figure 2:
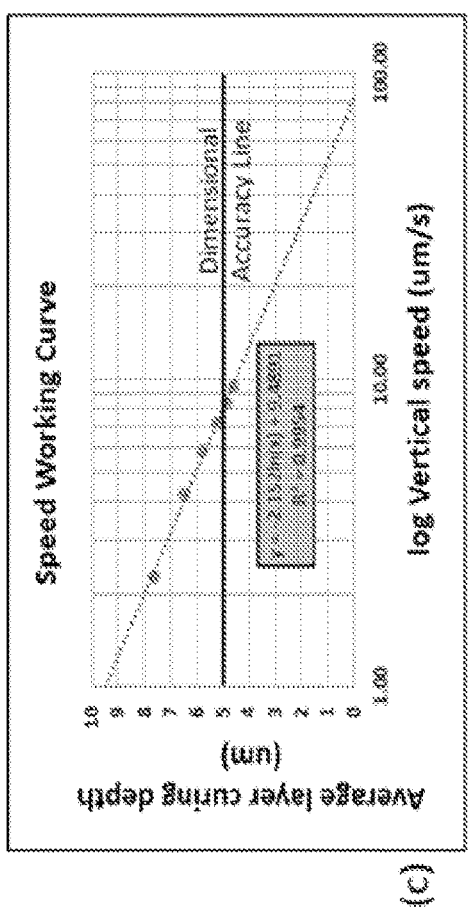

Experimental calibration of the Bone Scaffold Ink was performed with the microCLIP 3D printing system. FIGS. 2(a) and 2(b) show the CAD design and an SEM micrograph of the speed calibration structure, respectively. The calibration is performed by printing the calibration structure at a constant intensity while incrementally increasing the speed as each overhang is printed. The structure works to either experimentally determine where the print can be dimensionally accurate (average curing depth matches slicing thickness), and also gives curing depth profile in relation to UV intensity and speed. The curing depth profile can also be used to determine a theoretical maximum stage speed. FIG. 2(c) shows the experimentally determined speed working curve of the Bone Scaffold Ink. The trendline obtained for the speed working curve is in agreement with the General Form derived above. Information gained from this curve and trendline were used to determine the $v_c$, $E_c$, and to approximate the maximum dimensionally accurate speed with UV projected at full UV power (6.01 mW): 82.22 um/s, 0.2020 mJ/s, and 41.3 um/s, respectively.

Scaffold Fabrication

Figure 3:
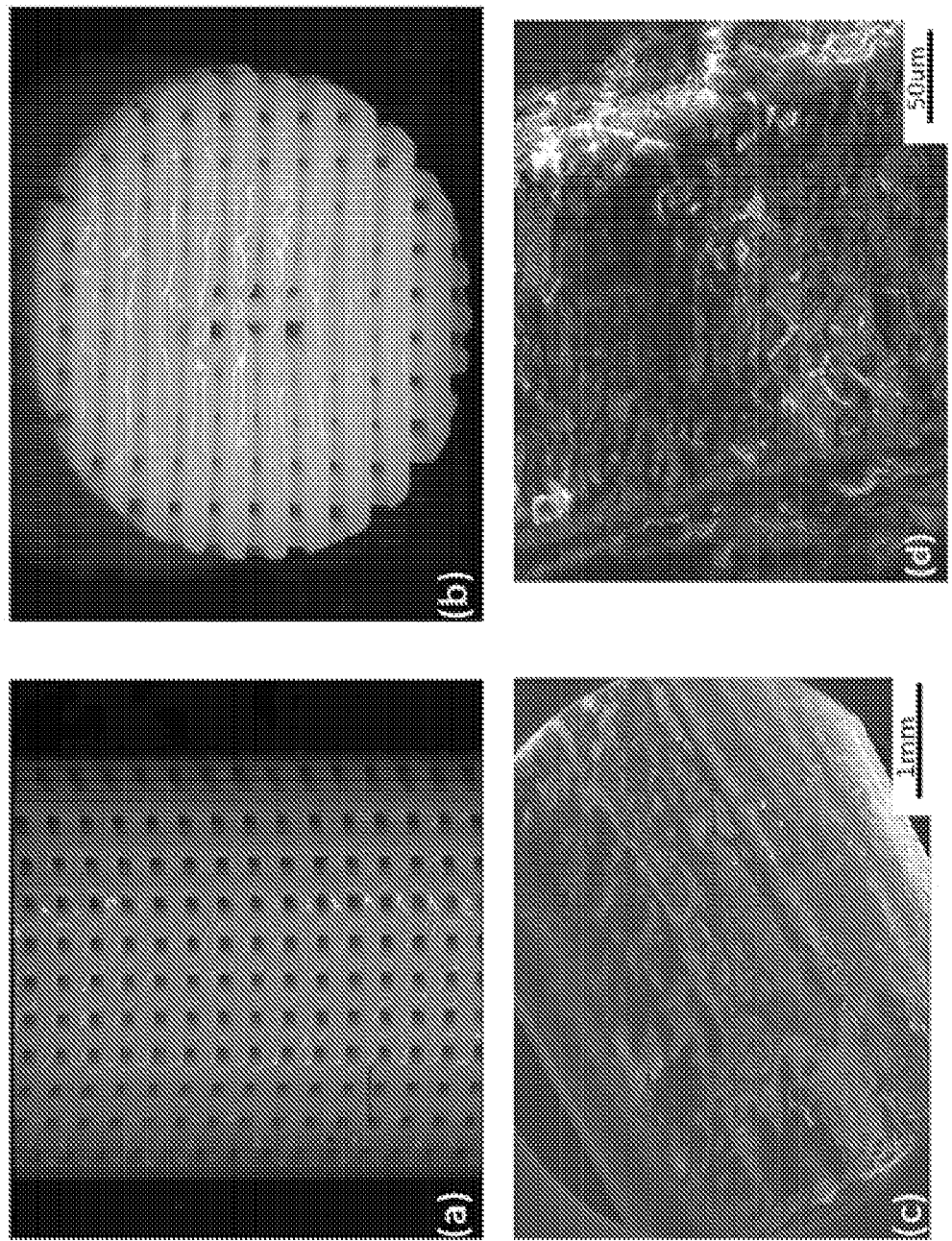
FIG. 3. (a) Side View Open Bone Scaffold. (b) Top view of Open Bone Scaffold. (c) SEM Side view of honeycomb cylinder. (d) SEM magnified top view of Open Bone Scaffold.

The "woodpile" bone scaffold design was fabricated with the following exposure conditions: UV intensity 1.15 mW/cm$^2$ (35% of maximum UV intensity), 11.7 um/s (vertical stage speed), 5 um layer slice thickness. These conditions were determined to be dimensionally accurate with the Speed Working Curve. Magnified views of the side and top are shown in FIGS. 3(a) and 3(b). Pictures were taken via the light microscope. SEM images of fabricated material are shown FIGS. 3(c) and 3(d). FIG. 3(c) is a side view of the honeycomb cylinder design, which was a solid wall. With CLIP there appears to be little evidence of "layering" traditionally seen in other 3D printing processes. FIG. 3(d) is a magnified view of the bone scaffold design.

Mechanical Properties Change with Time and Heat (4D-Capability)

Figure 4:
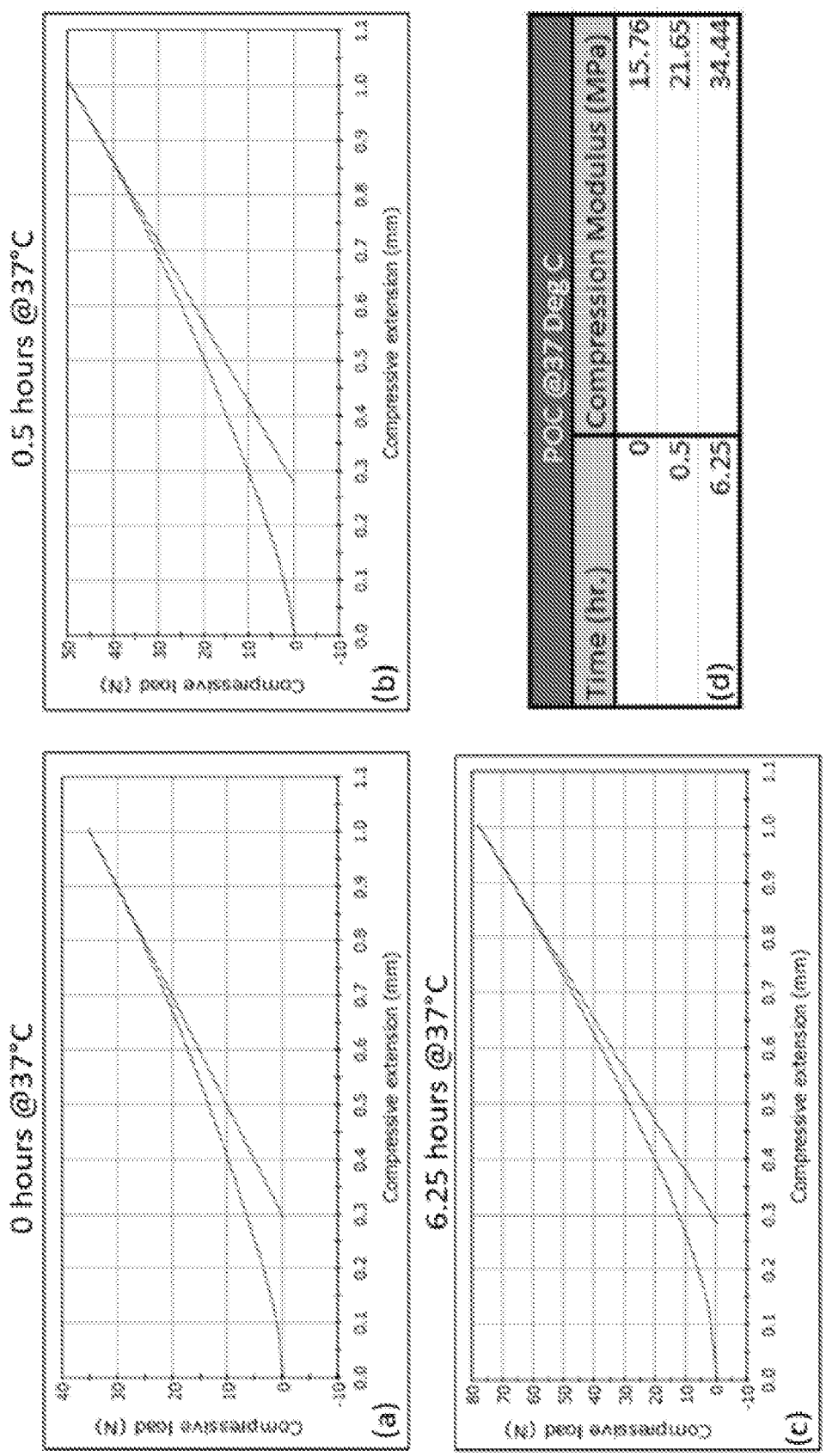
FIG. 4. Compression test results for 3D printed POC at various times of heating in 37° C. oven (a) 0 hours. (b) 0.5 hours. (c) 6.25 hours. (d) Corresponding Compression Moduli of tested mPOC tubes.

4D printing potential of the ink was investigated. The mPOC in the Bone Scaffold Ink is the photopolymerizable component of the composite. Methacrylated POC had previously been reported to be photopolymerizable, which makes mPOC (both individually and as part of the composite matrix) compatible with microCLIP and other stereolithography 3D printing processes (Ref. 9; incorporated by reference in its entirety). The component that was contemplated to make the composite ink 4D-capable is the thermally-induced radical initiator, V70. V70 is thermally induced to generate radicals near human body temperature. Methacrylated POC ink containing equal amounts photoinitiator and thermal initiator was observed to be 3D printable and with good quality. Photopolymerization appeared to be the dominant reaction rather than the thermal-induced polymerization reaction. FIG. 4 shows the compression test result plots of the 3 fabricated POC tubes.

Through compression testing, it was observed that exposure to the 37° C. caused additional polymerization in the fabricated structure. With increasing heating time, the compression modulus also increased. Parts made via stereolithography typically need some sort of post-processing to obtain final mechanical properties. This is typically performed via high intensity UV (flood) exposure or heat treatment performed at temperatures at or above 100° C. (Ref. 19; incorporated by reference in its entirety). Micro-CLIP allows the manufacture a "green" structure with set geometric boundaries and porosity. Introduction of V70 does not appear to heavily compete with the photoinitiator during 3D printing, which still allows good quality parts to be fabricated. The additional polymerization occurring at human body temperature allows the manufactured part to be press fit into place and gradually hardened to final properties over the course of several hours.

Multimaterial Printing Capability with microCLIP

Figure 5:
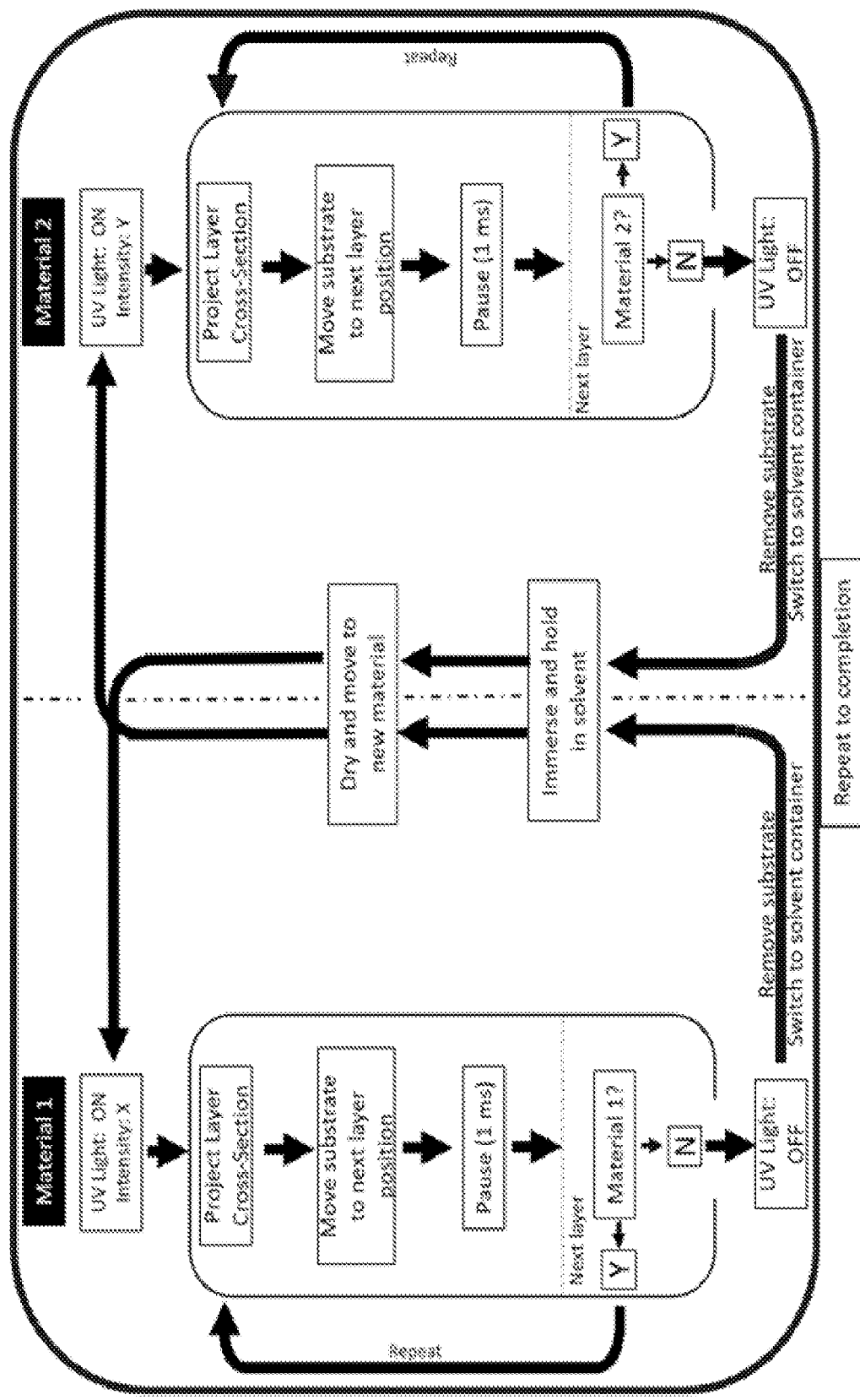
FIG. 5. Multimaterial printing process diagram for 2 materials.

Typical multi-material processes are performed using extrusion or poly-jet 3D printing methods. Stereolithography methods are normally seen as a single material process. There hasn't yet been any reported use of CLIP/microCLIP method for multiple material printing. While printing in CLIP is aimed to be continuous, with constant speed of the build platform, keeping the printing logic discretized more easily allows the ability to print with multiple materials. Each distinct material used in the multimaterial printing will have a different curing profile, so it is necessary to have flexibility to change UV intensity, build platform speed, and material bath within each fabrication layer. Shown in FIG. 5 is a process diagram of our multimaterial printing logic.

The printing logic of the microCLIP device is similar to a typical projection stereolithography printer. The command structure of a "bottom-up" PSL printer typically includes the following steps: project cross-section for specified amount of time, peel (or delaminate) fabricated layer from optical window, move build substrate to new position, pause for material to flow into voided area, repeat until part completion. This logic is discretized for each individual cross-sectional layer. The 3D fabrication logic largely keeps this discretized pattern, with the exception of no peel/delamination step and additional commands within each substep. Prior to any fabrication, each CAD design is sliced into cross-sections and a TXT file is created. This TXT file governs the stage vertical speed, stage distance to travel, UV light intensity, cross-section to project, and current material bath. The 3D printing logic for one material during the fabrication process, include the primary steps: Turn UV light on, project cross-section (throughout stage movement), move stage to next layer position, pause for cross-section change, project new cross section, repeat until part completion. UV light is active through entire part fabrication. While the logic is still discretized for each cross-sectional layer, the UV light is always projecting during the process which induces continuous polymerization through full fabrication. For multimaterial printing, the discretized nature of our printer logic works well. When switching to a new material, the program deactivates the UV, lifts the build-substrate, and moves the substrate into a solvent bath to clean uncured material from the fabricated part. Next, the build-substrate is raised and moved into the next material, UV is reactivated, and fabrication resumes. The build substrate travels with proper speed and device will project at proper UV intensity for dimensionally accurate curing of material 2.

Figure 6:
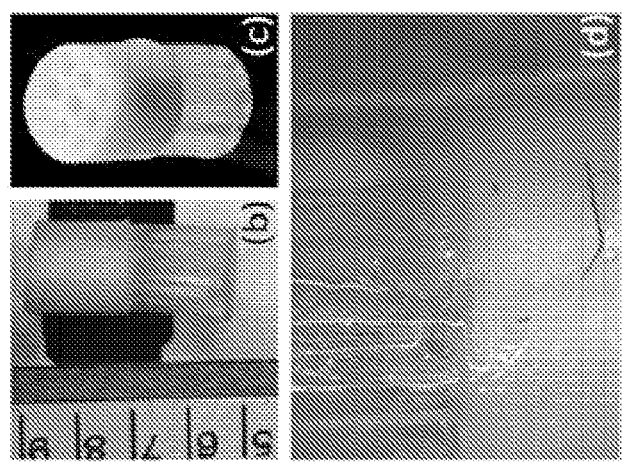
FIG. 6. Multimaterial printing utilizing microCLIP utilizing methacrylated poly 1,12 dodecanediol citrate (mPDDC) and HA/mPOC composite. (a) Diagram of microCLIP with multiple resin container s for multimaterial fabrication. (b) Side-view of multimaterial part. (c) Trimetric view of multimaterial part. (d) Magnified view of multimaterial part interface.
Figure 6:
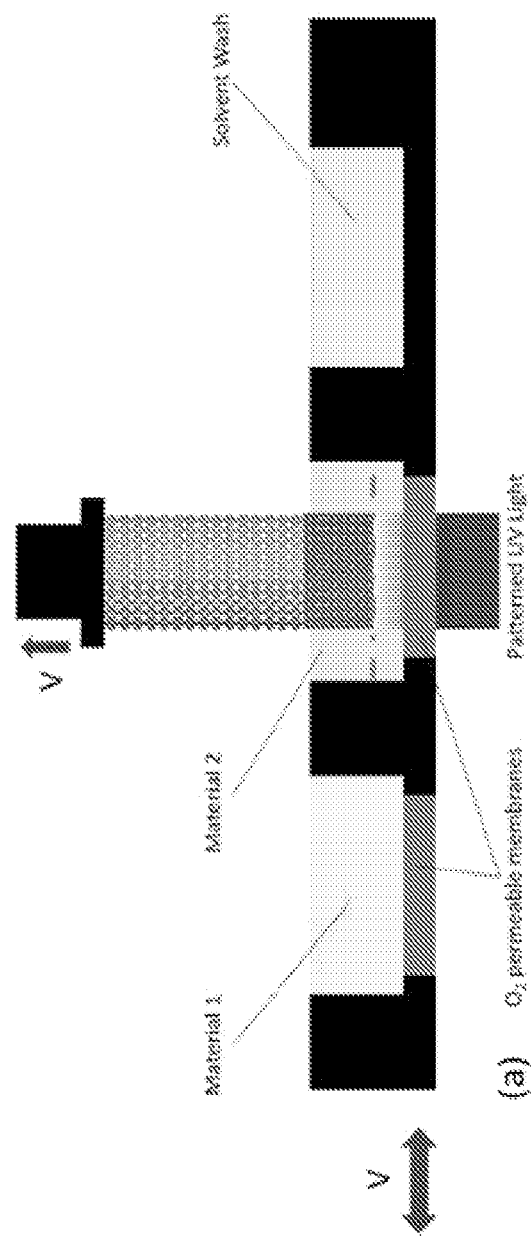

Shown in FIG. 6 is an example of multimaterial printing capabilities. FIG. 6(a) shows a diagram of the microCLIP with multimaterial bath. FIG. 6(b-d) shows various angles of a multimaterial part fabricated with microCLIP. Both materials fabricated the honeycomb cylinder design. Materials utilized were the mPDC, which has very good properties for soft tissue scaffolding and the Bone Scaffold Ink. This example has 2 distinct material regions. FIG. 6(d) shows the connecting region of mPDC and Bone Scaffold Ink. The regions are well connected, which implies cross linking between materials. As long as the material being utilized are compatible (acrylate to acrylate or epoxy to epoxy) this method works well. Fabrication of this multi-material part with 1 cm height was completed in 35 minutes. In this example, both photopolymerizable materials were CBBs with different monomer chain lengths. The ability to print with both a soft tissue scaffolding material and a bone tissue scaffolding material allows for efficient remodeling of all affected tissue.

Example 2

4D Print within POC Matrix mPOC tubes with 1 wt. % V70 were 3D printed via microCLIP and subjected to mechanical compression tests. Tube has inner diameter of 2.5 mm and outer diameter of 5.75 mm. The length of the tube is 16.5 mm. After printing, the tubes were placed in a convection oven at 37° C. for 0, 12, and 24 hours, to mimic the thermal-curing process at the body temperature. With increasing exposure to human body temperature, Maximum Force and Moduli increased. The as-printed (0 hr thermal-curing at 37° C.) tube had lowest modulus 1.31 MPa and lowest max force 2N. Tubes with 12-hour thermal-curing had an increased maximum force 78.53N and modulus 30.7 MPa. The full 24-hour exposure had the highest maximum force 140.48N and modulus of 100.23 MPa.

TABLE 1

Compression mechanical properties for 3D printed mPOC matrix material tubes with V70 co-initiator. Samples placed in 37° C. oven to determine effect of human body temperature on mechanical properties.

| Time @ 37° C. (hr) | Average Maximum Force (N) | Modulus (Automatic Young's) (MPa) | Compressive strain at Maximum Force (%) | Compressive stress at Maximum Force (MPa) |
|---|---|---|---|---|
| 0 | 2.00 | 1.31 | 15.15 | 0.16 |
| 12 | 78.53 | 30.70 | 30.00 | 6.29 |
| 24 | 140.48 | 100.23 | 24.62 | 11.68 |

Example 3

3D Printing Copper Ion-Infused POC Matrix to Promote Vascularization

Figure 7:
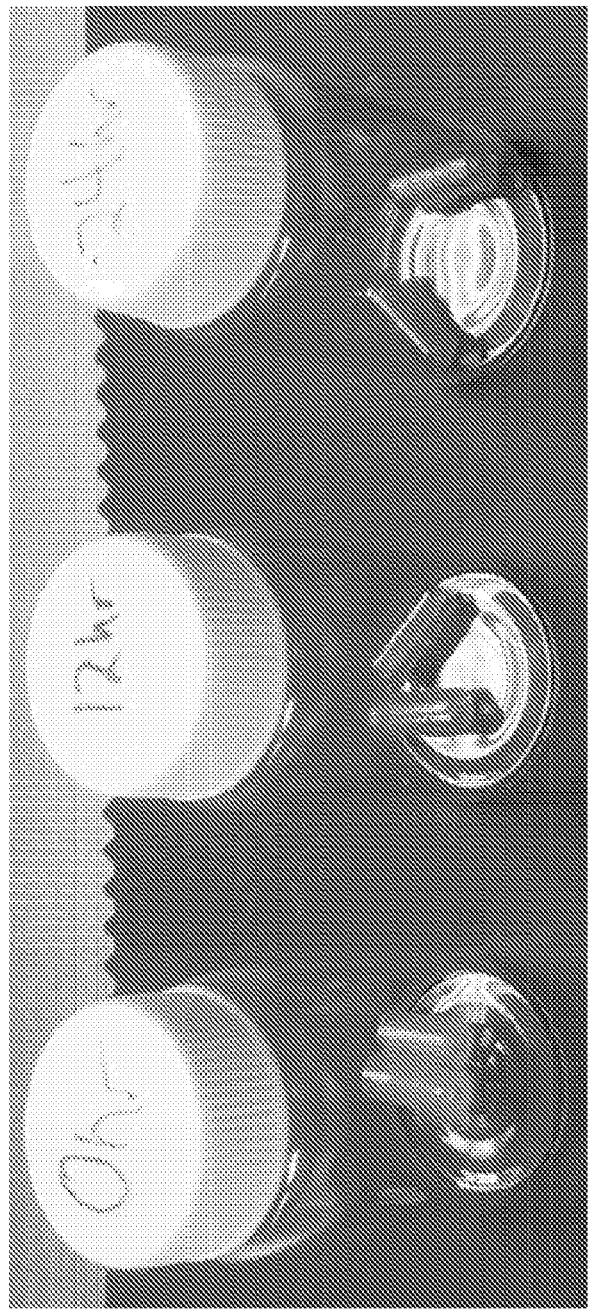
FIG. 7. 3D printed tubes from mPOC/Cu$^{2+}$ MOF ink. Tube has inner diameter of 2.5 mm and outer diameter of 5.75 mm. The length of the tube is 16.5 mm.

Various material additives or substitutions were tested for fabrication flexibility. Of key interest were use of $Cu^{2+}$ MOFs and Tricalcium Phosphate (TCP). Copper ion and drugs were of interest for promotion of vascularization. Feasibility fabrication tests were performed with mPOC and Copper metal organic frameworks (MOFs). A mixture of 82% mPOC, 1% Irgacure 819, 1% V70, 1% $Cu^{2+}$ MOF, and 15% EtOH was utilized in fabrication feasibility. It was observed that incorporation of $Cu^{2+}$ MOFs created a color change in the POC photopolymer from a clear yellow to a clear blue/green mixture. Tubes were printed with the following exposure conditions: 2.31 mW/cm² and 6.7 um/s. Printed tubes were able to be fabricated with reasonable dimensional fidelity. The incorporation of low % of MOFs did not introduce a significant lateral scattering effect. After printing, the tubes were placed in a convection oven at 37° C. for 0, 12, and 24 hours to characterize the thermal-curing characteristics (FIG. 7).

Example 4

Tricalcium Phosphate and Cu2+ MOFs

Figure 8:
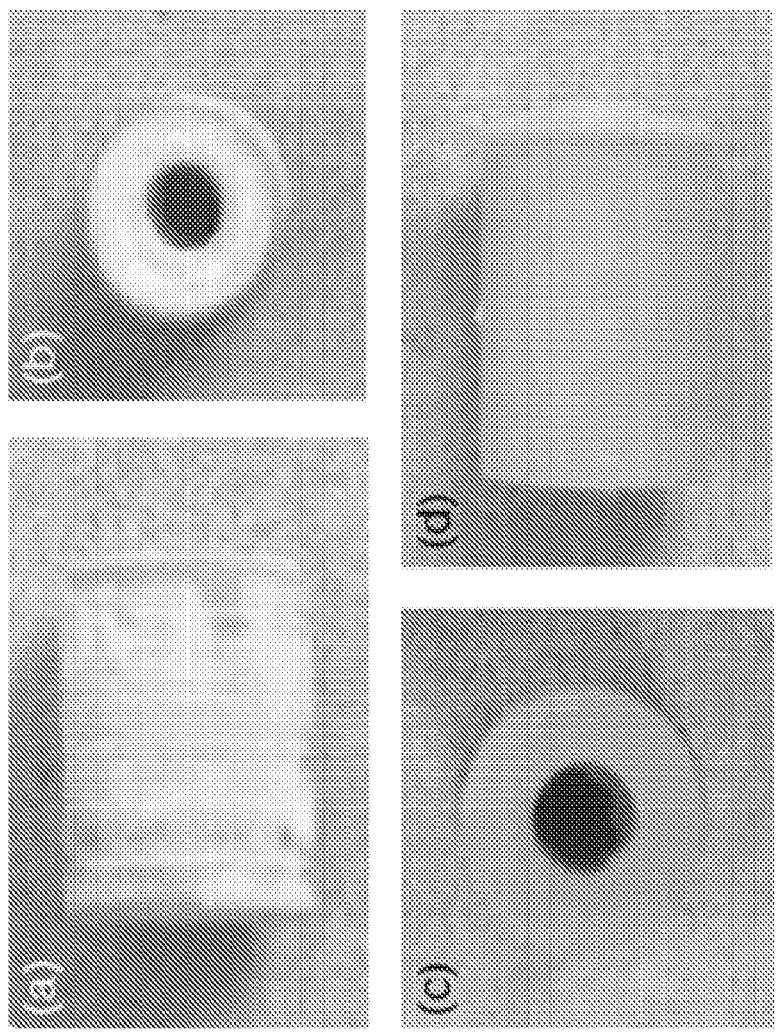
FIG. 8A-D. 3D printed tubes using mPOC/Cu$^{2+}$ MOF/TCP composite ink. (a) Sideview and (b) topview of tube printed using composite ink containing 4 um TCP microparticles. (a) Sideview and (b) topview of tube printed using composite ink containing 200 nm TCP nano-particles.

Following tests with mPOC and $Cu^{2+}$ MOFs, a composite ink containing 42% mPOC, 40% TCP micro-/nano-particles, 1% Irgacure 819, 1% V70, 1% $Cu^{2+}$ MOF, and 15% EtOH was prepared to test feasibility of printing. TCP is of interest over hydroxyapatite because of potential faster absorption within the body. 3D printing of this ink was experimentally tested to be feasible within microCLIP. Tubes were fabricated with exposure intensity density at 1.64 mW/cm² and printing speed of 4.75 um/s. Tubes showed excellent lateral dimensional fidelity. Inks with 4 um diameter TCP particles and 200 nm diameter TCP particles were compared for fabrication feasibility. Viscosity of fabrication inks were proportional to particle diameter, with 4 um particle ink having very high viscosity. 200 nm diameter TCP particle ink possessed very good particle distribution and lower viscosity than the 4 um TCP ink, allowing better printing quality. More uniform particle distribution required fabrication conditions to be slower (2.3068 mW/cm² and 3.33 um/s) than the 4 um TCP ink; however, final fabricated tubes from 200 nm TCP particle ink had better surface finish (FIG. 8).

REFERENCES

The following references, some of which are cited above by number, are herein incorporated by reference in their entireties.

1. Bose, S., M. Roy, and A. Bandyopadhyay, Recent advances in bone tissue engineering scaffolds. Trends in biotechnology, 2012. 30 (10): p. 546-554.
2. Jakus, A. E., et al., Hyperelastic "bone": A highly versatile, growth factor-free, osteoregenerative, scalable, and surgically friendly biomaterial. Science Translational Medicine, 2016. 8 (358): p. 358ra127-358ra127. 2.
3. Ameer, G., J. Yang, and R. Hoshi, Citric acid polymers. 2009, Google Patents.
5. David, L., L. Argenta, and D. Fisher, Hydroxyapatite cement in pediatric craniofacial reconstruction. Journal of Craniofacial Surgery, 2005. 16 (1): p. 129-133.
4. Qiu, H., et al., A citric acid-based hydroxyapatite composite for orthopedic implants. Biomaterials, 2006. 27 (34): p. 5845-5854.
6. Laurencin, C., Y. Khan, and S. F. El-Amin, Bone graft substitutes. Expert review of medical devices, 2014.
7. Tran, R. T., J. Yang, and G. A. Ameer, Citrate-based biomaterials and their applications in regenerative engineering. Annual review of materials research, 2015. 45: p. 277-310.
8. Yang, J., et al., Synthesis and evaluation of poly(diol citrate) biodegradable elastomers. Biomaterials, 2006. 27 (9): p. 1889-1898.
9. Wang, Y., M. R. Kibbe, and G. A. Ameer, Photo-crosslinked biodegradable elastomers for controlled nitric oxide delivery. Biomaterials science, 2013. 1 (6): p. 625-632.
10. Robert van Lith, E. B., Henry Ware, Jian Yang, Adam Cyrus Farsheed, Cheng Sun, and Guillermo Ameer, 3D-Printing Strong High Resolution Antioxidant Bioresorbable Vascular Stents. Advanced Materials Technologies, 2016.
11. Giannatsis, J. and V. Dedoussis, Additive fabrication technologies applied to medicine and health care: a review. The International Journal of Advanced Manufacturing Technology, 2009. 40 (1-2): p. 116-127.
12. Melchels, F. P., J. Feijen, and D. W. Grijpma, A review on stereolithography and its applications in biomedical engineering. Biomaterials, 2010. 31 (24): p. 6121-6130.

13. Kim, K., et al., Stereolithographic bone scaffold design parameters: osteogenic differentiation and signal expression. Tissue Engineering Part B: Reviews, 2010. 16 (5): p. 523-539.
14. Pei, E., 4D printing-revolution or fad? Assembly Automation, 2014. 34 (2): p. 123-127.
15. Sun, C., et al., Projection micro-stereolithography using digital micro-mirror dynamic mask. Sensors and Actuators A: Physical, 2005. 121 (1): p. 113-120.
16. John R. Tumbleston, D. S., Nikita Ermoshkin, Rima Janusziewicz, Ashley R. Johnson, David Kelly, Kai CHen, Robert Pinschmidt, Jason P. Rolland, Alexander Ermoshkin, Edward T. Samulski, Joseph M. DeSimone, Continuous Liquid Interface Production of 3D Objects. Science, 2015. 347 (6228): p. 1349-1352.
17. Ameer, G., H. Qiu, and J. Yang, Poly (diol co-citrate) hydroxyapatite composite for tissue engineering and orthapaedic fixation devices. 2013, Google Patents.
18. Bártolo, P. J., Stereolithography: materials, processes and applications. 2011: Springer Science & Business Media.
19. Jayanthi, S., B. Hokuf, and J. Lawton, Influence of Post Curing Conditions on the Mechanical Properties of Stereolithographic Photopolymers. Du Pont Somos Materials Group, August 1995.
20. Choi, J.-W., H.-C. Kim, and R. Wicker, Multi-material stereolithography. Journal of Materials Processing Technology, 2011. 211 (3): p. 318-328.
21. Wicker, R. B. and E. W. MacDonald, Multi-material, multi-technology stereolithography: This feature article covers a decade of research into tackling one of the major challenges of the stereolithography technique, which is including multiple materials in one construct. Virtual and Physical Prototyping, 2012. 7 (3): p. 181-194.

The invention claimed is:

1. A composition comprising:
    (a) an acrylated or methacrylated polymer of citric acid and linear aliphatic diol monomers;
    (b) a photoinitiator, wherein exposure to light of an appropriate wavelength results in formation of a first reactive species from the photoinitiator compound;
    (c) a thermal initiator, wherein exposure to heat results in in formation of a second reactive species from the thermal initiator compound; and
    (d) a copper (Cu) MOF.

2. The composition of claim 1, wherein the appropriate wavelength of light is in the UV range.

3. The composition of claim 1, further comprising one or more additional polymeric, bioceramic, metal organic framework (MOF), or nanostructured components.

4. The composition of claim 3, wherein the acrylated or methacrylated polymer and the additional component are present at a ratio of between 1:10 and 10:1.

5. The composition of claim 3, wherein the additional component is hydroxyapatite or tricalcium phosphate (TCP).

6. A composition comprising:
    (a) an acrylated or methacrylated polymer;
    (b) a photoinitiator, wherein exposure to light of an appropriate wavelength results in formation of a first reactive species from the photoinitiator compound; and
    (c) a thermal initiator, wherein exposure to heat results in in formation of a second reactive species from the thermal initiator compound, and
    (d) a copper (Cu) MOF.

7. The composition of claim 6, further comprising tricalcium phosphate (TCP).

8. The composition of claim 1, further comprising a solvent and/or wherein the composition is a liquid.

9. The composition of claim 1, wherein exposure of the composition to the light of an appropriate wavelength results in crosslinking of the acrylated or methacrylated polymer, induced by the photoinitiator, to form a malleable solid material, and wherein exposure of the malleable solid material to heat results in curing of the malleable solid material, induced by the thermal initiator, to form a thermoset material.

10. The composition of claim 6, wherein the acrylated or methacrylated polymer is a:
    (i) biodegradeable and/or biocompatible polyester;
    (ii) a citric acid-based polyester.

11. The composition of claim 10, wherein the citric acid-based polyester comprises of polymer of citric acid and linear aliphatic diol monomers.

12. The composition of claim 1, wherein the linear aliphatic diol monomers are selected from the group consisting of 1,4-butanediol, 1,6-hexanediol, 1,8-octanediol, 1,10-decanediol, 1,12-dodecanediol, 1,14-quattuordecanediol, and 1,16-sedecimanediol.

13. The composition of claim 1, wherein the photoinitiator comprises a compound selected from the group consisting of azobisisobutyronitrile (AIBN), benzoyl peroxide, 2,2-Dimethoxy-2-phenylacetophenone (DMPA), camphorquinone (CQ), phenylbis(2,4,6-trimethylbenzoyl) phosphine oxide (BAPO), 2-Hydroxy-2-methylpropiophenone, ethyl 4-dimethylaminobenzoate (EDAB), and 2-hydroxy-4'-(2-hydroxyethoxy)-2-methylpropiophenone.

14. The composition of claim 1, wherein the thermal initiator is selected from the group consisting of V-65, V-70, V-40, V-50, V-59, VA-044, VA-057, VA-061, VA-086, and BPO.

15. A method of stereolithographically printing a 3D object comprising:
    (a) depositing a layer of a composition comprising (i) an acrylated or methacrylated polymer of citric acid and linear aliphatic diol monomers, (ii) a photoinitiator, wherein exposure to light of an appropriate wavelength results in formation of a first reactive species from the photoinitiator compound, and (iii) a thermal initiator, wherein exposure to heat results in in formation of a second reactive species from the thermal initiator compound;
    (b) exposing the layer to light of the appropriate wavelength to form the first reactive species from the photoinitiator, wherein the first reactive species induces crosslinking of the acrylated or methacrylated polymer to form a malleable solid material;
    (c) depositing an additional layer of the composition of claim 1 atop the previous layer;
    (d) exposing the additional layer to light of the appropriate wavelength to form the first reactive species from the photoinitiator, wherein the first reactive species induces crosslinking of the acrylated or methacrylated polymer to form a malleable solid material; and
    (e) repeating steps (c) and (d) sufficient number of times to form the 3D object.

16. The method of claim 15, wherein the depositing and exposing steps are performed by continuous liquid interface processing (CLIP), microsterolithography, or microCLIP.

17. A method of curing an object produced by the method of claim 16 comprising:
    (a) manipulating the object into a desired shape; and
    (b) exposing the object to sufficient heat to form the second reactive species from the thermal initiator, wherein the second reactive species induces curing of the malleable solid material to cure the object in the desired shape.

* * * * *